United States Patent
Shelton et al.

(10) Patent No.: US 7,255,860 B2
(45) Date of Patent: *Aug. 14, 2007

(54) METHODS FOR TREATING POST-SURGICAL PAIN BY ADMINISTERING AN ANTI-NERVE GROWTH FACTOR ANTAGONIST ANTIBODY

(75) Inventors: David L. Shelton, Oakland, CA (US); German J. Vergara, Moraga, CA (US)

(73) Assignee: Rinat Neuroscience Corp., Palo Alto, CA (US)

( * ) Notice: Subject to any disclaimer, the term of this patent is extended or adjusted under 35 U.S.C. 154(b) by 142 days.

This patent is subject to a terminal disclaimer.

(21) Appl. No.: 10/682,638

(22) Filed: Oct. 8, 2003

(65) Prior Publication Data

US 2007/0160605 A1    Jul. 12, 2007

Related U.S. Application Data

(60) Provisional application No. 60/417,197, filed on Oct. 8, 2002.

(51) Int. Cl.
*A61K 39/395* (2006.01)
*C07K 16/22* (2006.01)
*C12P 21/06* (2006.01)

(52) U.S. Cl. .............................. 424/145.1; 424/130.1; 424/133.1; 530/387.1; 530/387.3; 530/388.24

(58) Field of Classification Search .................... None
See application file for complete search history.

(56) References Cited

U.S. PATENT DOCUMENTS

| | | | |
|---|---|---|---|
| 3,773,919 A | 11/1973 | Boswell et al. |
| 4,389,404 A | 6/1983 | Zhorov et al. |
| 4,485,045 A | 11/1984 | Regen |
| 4,544,545 A | 10/1985 | Ryan et al. |
| 4,676,980 A | 6/1987 | Segal et al. |
| 4,683,195 A | 7/1987 | Mullis et al. |
| 4,683,202 A | 7/1987 | Mullis |
| 4,754,065 A | 6/1988 | Levenson et al. |
| 4,777,127 A | 10/1988 | Suni et al. |
| 4,800,159 A | 1/1989 | Mullis et al. |
| 4,816,567 A | 3/1989 | Cabilly et al. |
| 5,013,556 A | 5/1991 | Woodle et al. |
| 5,047,335 A | 9/1991 | Paulson et al. |
| 5,130,311 A | 7/1992 | Guillaumet et al. |
| 5,147,294 A | 9/1992 | Smith et al. |
| 5,219,740 A | 6/1993 | Miller et al. |
| 5,278,299 A | 1/1994 | Wong et al. |
| 5,342,942 A | 8/1994 | Jaen et al. |
| 5,409,944 A | 4/1995 | Black et al. |
| 5,422,120 A | 6/1995 | Kim |
| 5,436,265 A | 7/1995 | Black et al. |
| 5,475,995 A | 12/1995 | Livingston |
| 5,500,362 A | 3/1996 | Robinson et al. |
| 5,510,261 A | 4/1996 | Goochee et al. |
| 5,510,368 A | 4/1996 | Lau et al. |
| 5,521,213 A | 5/1996 | Prasit et al. |
| 5,530,101 A | 6/1996 | Queen et al. |
| 5,536,752 A | 7/1996 | Ducharme et al. |
| 5,545,806 A | 8/1996 | Lonberg et al. |
| 5,545,807 A | 8/1996 | Surani et al. |
| 5,550,142 A | 8/1996 | Ducharme et al. |
| 5,552,422 A | 9/1996 | Gauthier et al. |
| 5,565,332 A | 10/1996 | Hoogenboom et al. |
| 5,569,825 A | 10/1996 | Lonberg et al. |
| 5,580,717 A | 12/1996 | Dower et al. |
| 5,580,859 A | 12/1996 | Felgner et al. |
| 5,585,089 A | 12/1996 | Queen et al. |
| 5,593,994 A | 1/1997 | Batt et al. |
| 5,604,253 A | 2/1997 | Lau et al. |
| 5,604,260 A | 2/1997 | Guay et al. |
| 5,616,601 A | 4/1997 | Khanna et al. |
| 5,625,126 A | 4/1997 | Lonberg et al. |
| 5,633,425 A | 5/1997 | Lonberg et al. |
| 5,639,780 A | 6/1997 | Lau et al. |
| 5,656,435 A | 8/1997 | Nakahama et al. |
| 5,661,016 A | 8/1997 | Lonberg et al. |
| 5,693,761 A | 12/1997 | Queen et al. |
| 5,693,762 A | 12/1997 | Queen et al. |
| 5,712,100 A | 1/1998 | Nakahama et al. |
| 5,733,743 A | 3/1998 | Johnson et al. |

(Continued)

FOREIGN PATENT DOCUMENTS

| | | |
|---|---|---|
| EP | 0 345 242 | 12/1989 |
| EP | 0 418 590 A1 | 3/1991 |
| EP | 0 418 590 B1 | 3/1991 |
| EP | 0 519 596 | 12/1992 |
| EP | 0 524 968 | 2/1993 |
| FR | 2 807 660 A1 | 10/2001 |

(Continued)

OTHER PUBLICATIONS

Gwak et al. (2003). Attenuation of mechanical hyperalgesia following spinal cord injury by administration of antibodies to nerve growth factor in rat. Neuroscience Letters. 336:117-120.*

Zahn et al. (2004). Effect of blockade of nerve growth factor and tunor necrosis factor on pain behaviors after plantar incision. The Journal of Pain. 5(3):157-163.*

Brennan, T.J. (1999). Postoperative models of nociception. ILAR Journal. 40(3):129-136.*

McMahon et al. (1995). The biological effects of endogenous nerve growth factor on adult sensory neurons revealed by a trkA-IgG fusion molecule. Nature Medicine. 1(8):774-780.*

(Continued)

*Primary Examiner*—Christine J. Saoud
*Assistant Examiner*—Jon M. Lockard
(74) *Attorney, Agent, or Firm*—Philip B. Polster, II

(57) ABSTRACT

The invention features methods and compositions for preventing or treating post-surgical pain by administering an anti-NGF antagonist antibody.

11 Claims, 9 Drawing Sheets

U.S. PATENT DOCUMENTS

| | | |
|---|---|---|
| 5,750,373 A | 5/1998 | Garrard et al. |
| 5,766,863 A | 6/1998 | Godowski et al. |
| 5,807,715 A | 9/1998 | Morrison et al. |
| 5,814,482 A | 9/1998 | Dubensky, Jr. et al. |
| 5,821,337 A | 10/1998 | Carter et al. |
| 5,843,942 A | 12/1998 | Breault et al. |
| 5,844,092 A | 12/1998 | Presta et al. |
| 5,866,692 A | 2/1999 | Shitara et al. |
| 5,877,016 A | 3/1999 | Presta et al. |
| 5,891,650 A | 4/1999 | Godowski et al. |
| 5,981,568 A | 11/1999 | Kunz et al. |
| 5,997,867 A | 12/1999 | Waldmann et al. |
| 6,017,878 A | 1/2000 | Saragovi et al. |
| 6,022,875 A | 2/2000 | Zimmer et al. |
| 6,027,927 A | 2/2000 | Presta et al. |
| 6,054,297 A | 4/2000 | Carter et al. |
| 6,127,401 A | 10/2000 | Singh et al. |
| 6,153,189 A | 11/2000 | Presta et al. |
| 6,180,370 B1 | 1/2001 | Queen et al. |
| 6,180,377 B1 | 1/2001 | Morgan et al. |
| 6,210,671 B1 | 4/2001 | Co |
| 6,265,150 B1 | 7/2001 | Terstappen et al. |
| 6,291,247 B1 | 9/2001 | Riopelle et al. |
| 6,306,849 B1 | 10/2001 | Hudkins et al. |
| 6,331,415 B1 | 12/2001 | Cabilly et al. |
| 6,350,861 B1 | 2/2002 | Co et al. |
| 6,359,130 B1 | 3/2002 | Singh et al. |
| 6,376,471 B1 | 4/2002 | Lawrence, III et al. |
| 6,399,780 B1 | 6/2002 | Hudkins |
| 6,413,942 B1 | 7/2002 | Felgner et al. |
| 6,436,908 B1 | 8/2002 | Koch et al. |
| 6,492,380 B1 | 12/2002 | Ross et al. |
| 6,506,559 B1 | 1/2003 | Fire et al. |
| RE38,103 E | 4/2003 | Guay et al. |
| 6,548,062 B2 | 4/2003 | Buchkovich et al. |
| 6,548,640 B1 | 4/2003 | Winter |
| 6,649,605 B2 | 11/2003 | Olesen et al. |
| 6,919,426 B2 | 7/2005 | Boone et al. |
| 2001/0046959 A1 | 11/2001 | Buchovich et al. |
| 2002/0028779 A1 | 3/2002 | High et al. |
| 2002/0072543 A1 | 6/2002 | Olesen et al. |
| 2002/0146416 A1 | 10/2002 | Presta et al. |
| 2003/0008807 A1 | 1/2003 | Levine et al. |
| 2003/0072746 A1 | 4/2003 | Miller |
| 2003/0203923 A1 | 10/2003 | Ross et al. |
| 2004/0038874 A1 | 2/2004 | Omoigui |
| 2004/0071701 A1 | 4/2004 | Delafoy et al. |
| 2004/0097562 A1 | 5/2004 | Olesen et al. |
| 2004/0121959 A1 | 6/2004 | Boone et al. |
| 2004/0131615 A1 | 7/2004 | Shelton et al. |
| 2004/0228862 A1 | 11/2004 | Shelton et al. |
| 2004/0237124 A1 | 11/2004 | Pons et al. |
| 2004/0253244 A1 | 12/2004 | Shelton et al. |
| 2005/0074821 A1 | 4/2005 | Wild, Jr. et al. |
| 2005/0222035 A1 | 10/2005 | Boone et al. |
| 2005/0265994 A1 | 12/2005 | Shelton et al. |

FOREIGN PATENT DOCUMENTS

| | | |
|---|---|---|
| GB | 2200651 | 8/1988 |
| JP | 63-295588 A | 12/1988 |
| JP | 03-163905 A | 7/1991 |
| JP | 05-076384 A | 3/1993 |
| JP | 06-317587 A | 11/1994 |
| WO | WO 87/04462 | 7/1987 |
| WO | WO 89/09225 | 10/1989 |
| WO | WO 90/07936 | 7/1990 |
| WO | WO-90/10644 A1 | 9/1990 |
| WO | WO 90/11092 | 10/1990 |
| WO | WO 91/00360 | 1/1991 |
| WO | WO 91/02805 | 3/1991 |
| WO | WO 91/14445 | 10/1991 |
| WO | WO 92/20373 | 11/1992 |
| WO | WO 93/03769 | 3/1993 |
| WO | WO 93/06213 | 4/1993 |
| WO | WO 93/10218 | 5/1993 |
| WO | WO 93/11230 | 6/1993 |
| WO | WO 93/19191 | 9/1993 |
| WO | WO 93/25234 | 12/1993 |
| WO | WO 93/25698 | 12/1993 |
| WO | WO 94/03622 | 2/1994 |
| WO | WO 94/04690 | 3/1994 |
| WO | WO 94/12649 | 6/1994 |
| WO | WO 94/23697 | 10/1994 |
| WO | WO 94/28938 | 12/1994 |
| WO | WO 95/00655 | 1/1995 |
| WO | WO 95/07994 | 3/1995 |
| WO | WO 95/11984 | 5/1995 |
| WO | WO 95/13796 | 5/1995 |
| WO | WO-95/25795 A1 | 9/1995 |
| WO | WO 95/30763 | 11/1995 |
| WO | WO 96/17072 | 6/1996 |
| WO | WO 97/15593 | 5/1997 |
| WO | WO 97/21732 | 6/1997 |
| WO | WO 97/42338 | 11/1997 |
| WO | WO 98/06048 | 2/1998 |
| WO | WO 98/17278 | 4/1998 |
| WO | WO-98/19674 A2 | 5/1998 |
| WO | WO-98/19674 A3 | 5/1998 |
| WO | WO 99/53055 | 10/1999 |
| WO | WO 99/58572 | 11/1999 |
| WO | WO 00/53211 | 9/2000 |
| WO | WO 00/69829 | 11/2000 |
| WO | WO 00/73344 | 12/2000 |
| WO | WO 01/27160 | 4/2001 |
| WO | WO 01/29058 | 4/2001 |
| WO | WO-01/52843 A1 | 7/2001 |
| WO | WO 01/64247 | 9/2001 |
| WO | WO 01/78698 | 10/2001 |
| WO | WO 01/92513 | 12/2001 |
| WO | WO 02/15924 | 2/2002 |
| WO | WO 02/17914 | 3/2002 |
| WO | WO 02/20479 | 3/2002 |
| WO | WO-02/20513 A1 | 3/2002 |
| WO | WO 02/44321 | 6/2002 |
| WO | WO 02/96458 | 12/2002 |
| WO | WO-02/102232 A2 | 12/2002 |
| WO | WO-02/102232 A3 | 12/2002 |
| WO | WO-03/022261 A1 | 3/2003 |
| WO | WO-2004/026329 A1 | 4/2004 |
| WO | WO-2004/028448 A2 | 4/2004 |
| WO | WO-2004/028448 A3 | 4/2004 |
| WO | WO-2004/032852 A2 | 4/2004 |
| WO | WO-2004/032852 A3 | 4/2004 |
| WO | WO-2004/032870 A2 | 4/2004 |
| WO | WO-2004/032870 A3 | 4/2004 |
| WO | WO-2004/058184 A2 | 7/2004 |
| WO | WO-2004/065560 A2 | 8/2004 |
| WO | WO-2004/073653 A2 | 9/2004 |
| WO | WO-2004/096122 A2 | 11/2004 |
| WO | WO-2005/000194 A2 | 1/2005 |
| WO | WO-2005/000194 A3 | 1/2005 |
| WO | WO-2005/019266 A2 | 3/2005 |
| WO | WO-2005/019266 A3 | 3/2005 |
| WO | WO-2005/111077 A2 | 11/2005 |
| WO | WO-2005/111077 A3 | 11/2005 |

OTHER PUBLICATIONS

Jarvis et al. (2002). A-317491, a novel potent and selective non-nucleotide antagonist of P2X3 and P2X2/3 receptors, reduces chronic inflammatory and neuropathic pain in the rat. Proc. Natl. Acad. Sci. USA 99(26):17179-17184.*

Joshi et al. (2006). Involvement of the TTX-resistant sodium channel Nav 1.8 in inflammatory and neuropathic, but not postoperative pain states. Pain. 123:75-82.*
U.S. Appl. No. 10/682,331, filed Oct. 8, 2003, Shelton et al.
U.S. Appl. No. 10/682,332, filed Oct. 8, 2003, Shelton et al.
U.S. Appl. No. 10/745,775, filed Dec. 24, 2003, Pons et al.
U.S. Appl. No. 10/783,730, filed Feb. 19, 2004, Shelton et al.
U.S. Appl. No. 10/791,162, filed Mar. 1, 2004, Shelton et al.
Adey, N.B. et al. (1996). "Preparation of Second-Generation Phage Libraries" Chapter 16 In Phage Display of Peptides and Proteins: A Laboratory Manual Kay, B.K. et al. eds. Academic Press, Inc.: San Diego, CA pp. 277-291.
Agrawal, S. et al. (1998). "Mixed Backbone Oligonucleotides: Improvement in Oligonucleotide-Induced Toxicity In Vivo," Antisense & Nucleic Acid Drug Development 8:135-139.
Aley, K.O. et al. (1996). "Delayed Sympathectomy After a Prolonged Hyperalgesia Results in a Subsequent Enhanced Acute Hyperalgesic Response," Neuroscience 71(4):1083-1090.
Al-Lazikani, B. et al. (1997). "Standard Conformations for the Canonical Structures of Immunoglobulins," J. Molec. Biol. 273:927-948.
Aloe, L. et al. (1992). "Nerve Growth Factor and Distribution of Mast Cells in the Synovium of Adult Rats," Clin. Exp. Rheumatol. 10:203-204.
Aloe, L. et al. (1992). "Nerve Growth Factor in the Synovial Fluid of Patients with Chronic Arthritis," Arch. Rheum. 35(3):351-355.
Aloe, L. et al. (1993). "Level of Nerve Growth Factor and Distribution of Mast Cells in the Synovium of Tumour Necrosis Factor Transgenic Arthritic Mice," Int. J. Tissue Reactions 15(4):139-143.
Aloe, L. et al. (1995). "Effect of NGF Antibodies on Mast Cell Distribution, Histamine and Substance P Levels in the Knee Joint of TNF-Arthritic Transgenic Mice," Rheumatol. Int. 14:249-252.
Amann, R. et al. (1996). "Intraplantar Injection of Nerve Growth Factor into the Rat Hind Paw: Local Adema and Effects on Thermal Nociceptive Threshold," Pain 64:323-329.
Andreev, N.Y. et al. (1995). "Peripheral Administration of Nerve Growth Factor in the Adult Rat Produces a Thermal Hyperalgesia that Requires the Presence of Sympathetic Post-Ganglionic Neurones," Pain 63:109-115.
Apfel, S.C. et al. (1996). "Nerve Growth Factor Regulates the Expression of Brain-Derived Neurotrophic Factor mRNA in the Peripheral Nervous System," Mol. Cell. Neurosci 7:134-142.
Armour, K. L. et al. (1999). "Recombinant Human IgG Molecules Lacking Fcγ Receptor I Binding and Monocyte Triggering Activities," Eur. J. Immunol. 29:2613-2624.
Balint, R. F. et al. (1993). "Antibody Engineering By Parsimonious Mutagenesis," Gene 137:109-118.
Bird, R.E. et al. (1988). "Single-Chain Antigen-Binding Proteins," Science 242:423-426.
Bischoff, S.C. et al. (1992). "Effect of Nerve Growth Factor on the Release of Inflammatory Mediators by Mature Human Basophils," Blood 79(10):2662-2669.
Boerner, P. et al. (1991). "Production of Antigen-Specific Human Monoclonal Antibodies From In Vitro-Primed Human Splenocytes," J. Immunol. 147(1):86-95.
Boettger, M.K. et al. (2002). "Calcium-Activated Potassium Channel SK1—and IK1-like Immunoreactivity in Injured Human Sensory Neurones and its Regulation by Neurotrophic Factors," Brain 125:252-263.
Borsani, G. et al. (1990). "cDNA Sequence of Human β-NGF," Nuc. Acids Res. 18(13):4020.
Boyd, P.N. et al. (1996). "The Effect of the Removal of Sialic Acid, Galactose and Total Carbohydrate on the Functional Activity of Campath-1H," Mol. Immunol. 32(17/18):1311-1318.
Bracci Laudiero, L. et al. (1992). "Multiple Sclerosis Patients Express Increased Levels of β-Nerve Growth Factor in Cerebrospinal Fluid," Neurosci Lett. 147:9-12.
Bracci-Laudiero, L. et al. (1993). "Increased Levels of NGF in Sera of Systemic Lupus Erythematosus Patients," Neuroreport 4(5):563-565.
Braun, A. et al. (1998). "Role of Nerve Growth Factor in a Mouse Model of Allergic Airway Inflammation and Asthma," Eur. J. Immunol. 28:3240-3251.

Brennan, T.J. et al. (1996). "Characterization of a Rat Model of Incisional Pain," Pain 64:493-501.
Brennan, T.J. et al. (1998). "Role of Nerve Growth Factor in a Rat Model for Postoperative Pain," Society for Neuroscience Abstracts 28th Annual Meeting, Los Angeles, CA, Nov. 7-12, 1998, 24(1):880. Abstract No. 349.4.
Brown, B.A. et al. (1987). "Tumor-Specific Genetically Engineered Murine/Human Chimeric Monoclonal Antibody," Cancer Res. 47:3577-3583.
Buchman, V.L. et al. (1993). "Different Neurotrophins are Expressed and Act in a Developmental Sequence to Promote the Survival of Embryonic Sensory Neurons," Development 118:989-1001.
Buck, D.W. et al. (1982). "Monoclonal Antibodies Specific For Cells Culture Mycoplasmas," In Vitro 18(4):377-381.
Capel, P.J.A. et al. (1994). "Heterogeneity of Human IgG Fc Receptors," Immunomethods 4:25-34.
Caraceni, A. et al. (2002). "Pain Measurement Tools and Methods in Clinical Research in Palliative Care: Recommendations of an Expert Working Group of the European Association of Palliative Care," J. Pain Symptom. Manage. 23(3):239-255.
Chao, M.V. et al. (1986). "Gene Transfer and Molecular Cloning of the Human NGF Receptor," Science 232:518-521.
Chiou, H.C. et al. (1994). "In Vivo Gene Therapy via Receptor-Mediated DNA Delivery," In Gene Therapeutics: Methods and Applications of Direct Gene Transfer J.A. Wolff, ed. Birkhauser, pp. 143-156.
Chothia, C. et al. (1989). "Conformations of Immunoglobulin Hypervariable Regions," Nature 342:877-883.
Chuang, H-H. et al. (2001). "Bradykinin and Nerve Growth Factor Release the Capsaicin Receptor From PtdIns(4,5)$P_2$-Mediated Inhibition," Nature 411:957-962.
Chun, L.L.Y. et al. (1977). "Role of Nerve Growth Factor in the Development of Rat Sympathetic Neurons in Vitro," The Journal of Cell Biology. 75:705-711.
Clackson, T. et al. (1991). "Making Antibody Fragments Using Phage Display Libraries," Nature 352:624-628.
Clynes, R. et al. (1998). "Fc Receptors Are Required in Passive and Active Immunity to Melanoma," Proc. Natl. Acad. Sci. USA 95:652-656.
Cole, S.P.C. et al. (1985). "The EBV-Hybridoma Technique and Its Application to Human Lung Cancer" In Monoclonal Antibodies and Cancer Therapy, Reisfeld, R. et al. eds., Alan R. Liss, Inc.: New York, NY, pp. 77-96.
Connelly, S. et al. (1995). "In Vivo Gene Delivery and Expression of Physiological Levels of Functional Human Factor VIII in Mice," Human Gene Therapy 6:185-193.
Crowley, C. et al. (1994). "Mice Lacking Nerve Growth Factor Display Perinatal Loss of Sensory and Sympathetic Neurons yet Develop Basal Forebrain Cholinergic Neruons," Cell 76:1001-1011.
Curiel, D.T. et al. (1992). "High-Efficiency Gene Transfer Mediated by Adenovirus Coupled to DNA-Polylysine Complexes," Hum. Gene Ther. 3:147-154.
Daugherty, B.L. et al. (1991). "Polymerase Chain Reaction Facilitates the Cloning, CDR-Grafting, and Rapid Expression of a Murine Monoclonal Antibody Directed Against the CD18 Component of Leukocyte Integrins," Nucl. Acids Res. 19(9):2471-2476.
Dayhoff, M.O. ed. (1978). "A Model of Evolutionary Change in Proteins" Chapter 22 In Atlas of Protein Sequence and Structure National Biomedical Research Foundation, Washington D.C. 5(Supp.3):345-352.
deHaas, M. et al. (1995), "Fcα Receptors of Phagocytes," J. Lab. Clin. Med. 126:330-341.
DeKock, M. et al. (2001). "Balanced Analgesia' in the Perioperative Period: Is There a Place for Ketamine?" Pain 92:373-380.
DiMarco, E. et al. (1993). "Nerve Growth Factor Binds to Normal Human Keratinocytes Through High and Low Affinity Receptors and Stimulates Their Growth by a Novel Autocrine Loop," J. Biol. Chem. 268(30):22838-22846.
Dyck, P.J. et al. (1997). "Intradermal Recombinant Human Nerve Growth Factor Induces Pressure Allodynia and Lowered Heat-Pain Threshold in Humans," Neurology 48:501-505.

Eide, F.F. et al. (1996). "Naturally Occurring Truncated trkB Receptors Have Dominant Inhibitory Effects on Brain-Derived Neurotrophic Factor Signaling," *J. Neurosci.* 16(10):3123-3129.

Eppstein, D.A. et al. (1985). "Biological Activity of Liposome-Encapsulated Murine Interferon y is Mediated by a Cell Membrane Receptor," *Proc. Natl. Acad. Sci. USA* 82:3688-3692.

Falcini, F. et al. (1996). "Increased Circulating Nerve Growth Factor is Directly Correlated with Disease Activity in Juvenile Chronic Arthritis," *Ann. Rheum. Dis.* 55:745-748.

Felson, D.T. et al. (1993). "The American College of Rheumatology Preliminary Core Set of Disease Activity Measures For Rheumatoid Arthritis Clinical Trial," *Arthritis and Rheumatism* 36(6):729-740.

Findeis, M.A. et al. (1993). "Targeted Delivery of DNA for Gene Therapy Via Receptors," *Trends Biotechnol.* 11:202-205.

Foster, P.A. et al. (2002). "Cellular Pathology Changes in Rat Skin Following Intradermal Injection of Nerve Growth Factor: Neutrophil-Dependent and -Independent Events," *J. Pathol.* 197:245-255.

Fries, J.F. et al. (1982). "The Dimensions of Health Outcomes: The Health Assessment Questionnaire, Disability and Pain Scales," *J. Rheumatol.* 9(5):789-793.

Gazzano-Santoro, H. et al. (1996). "A Non-Radioactive Complement-Dependent Cytotoxicity Assay For Anti-CD20 Monoclonal Antibody," *J. Immunol. Methods* 202:163-171.

GenBank Accession No. L17077, "The Use of the RACE Method to Clone Hybridoma cDNA When V Region Primers Fail," created on Feb. 7, 1995, located at <http://www.ncbi.nih.gov>, last visited on Mar. 18, 2004, two pages.

GenBank Accession No. L17078, "The Use of the RACE Method to Clone Hybridoma cDNA When V Region Primers Fail," created on Feb. 7, 1995, located at <http://www.ncbi.nih.gov>, last visited on Mar. 18, 2004, one page.

GenBank Accession No. NM_002506, "Histamne Enhances the Production of Nerve Growth Factor in Human Keratinocytes," created on Dec. 23, 2003, located at <http://www.ncbi.nih.gov>, last visited on Jun. 11, 2004, four pages.

GenBank Accession No. U39608, "Two Distinct Monoclonal Antibodies Raised Against Mouse Beta Nerve Growth Factor: Generation of Bi-Specific Anti-Nerve Growth Factor Anti-Horseradish Peroxidase Antibodies for Use in a Homogenous Enzyme Immunoassay," created on Mar. 25, 1999, located at <http://www.ncbi.nih.gov>, last visited on Mar. 18, 2004, two pages.

GenBank Accession No. U39609, "Two Distinct Monoclonal Antibodies Raised Against Mouse Beta Nerve Growth Factor: Generation of Bi-Specific Anti-Nerve Growth Factor Anti-Horseradish Peroxidase Antibodies for Use in a Homogenous Enzyme Immunoassay," created Jan. 28, 1999, located at <http://www.ncbi.nih.gov>, last visited on Mar. 18, 2004, two pages.

Gerstenfeld, L.C. et al. (2003). "Differential Inhibition of Fracture Healing by Non-Selective and Cyclooxygenase-2 Selective Non-Steroidal Anit-Inflammatory Drugs," *J. Orthop. Res.* 21:670-675.

Gould, H.J. III et al. (2000). "A Possible Role for Nerve Growth Factor in the Augmentation of Sodium Channels in Models of Chronic Pain," *Brain Res.* 854:19-29.

Griffiths, A.D. et al. (1993). "Human Anti-Self Antibodies with High Specificity From Phage Display Libraries," *EMBO J.* 12(2):725-734.

Guyer, R.L. et al. (1976). "Immunoglobulin Binding by Mouse Intestinal Epithelial Cell Receptors," *J. Immunol.* 117(2):587-593.

Hains, B.C. et al. (2002). "Differential Electrohysiological Effecs of Brain-Derived Neurotrophic Factor on Dorsal Horn Neurons Following Chronic Spinal Cord Hemisection Injury in the Rat," *Neurosci Lett.* 320:125-128.

Haws, M.J. et al. (1996). "The Effects of Chronic Ketorolac Tromethamine (Toradol) On Wound Healing," *Ann. Plas. Surg.* 37:147-151.

Hein, J. (1990). "Unified Approach to Alignment and Phylogenes" Chapter 39 *In Methods in Enzymology* Academic Press, Inc.: San Diego, CA 183:626-645.

Higgins, D.G. et al. (1998). "Fast and Sensitive Multiple Sequence Alignments on a Microcomputer," *CABIOS Communications* 5(2):151-153.

Higuchi, R. (1990). "Recombinant PCR" Chapter 22 *In PCR Protocols: A Guide to Methods and Applications* Innis, M.A. et al. eds. Academic Press, Inc., pp. 177-183.

Holliger, P. et al. (1993). "'Diabodies': Small Bivalent and Bispecific Antibody Fragments," *Proc. Natl. Acad. Sci. USA* 90:6444-6448.

Hongo, J. S. et al. (2000). "Antibody Binding Regions on Human Nerve Growth Factor Identified by Homolog- and Alanine-Scanning Mutagenesis," *Hybridoma* 19(3):215-227.

Hoogenboom, H. R. et al. (1991). "By-Passing Immunisation: Human Antibodies From Synthetic Repertoires of Germline $V_H$ Gene Segments Rearranged in Vitro," *J. Mol. Biol.* 227:381-388.

Horigome, K. et al. (1993). "Mediator Release from Mast Cells by Nerve Growth Factor," *J. Biol. Chem.* 268(20):14881-14887.

Hsu, T-A. et al. (1997). "Differential *N*-Glycan Patterns of Secreted and Intracellular IgG Produced in *Trichoplusia ni* Cells," *J. Biol. Chem.* 272(14):9062-9070.

Hwang, K.J. et al. (1980). "Hepatic Uptake and Degradation of Unilamellar Sphingomyelin/Cholesterol Liposomes: A Kinetic Study," *Proc. Natl. Acad. Sci. USA* 77(7):4030-4034.

Iannone, F. et al. (2002). "Increased Expression of Nerve Growth Factor (NGF) and High Affinity NGF Receptor (p140 TrkA) in Human Osteoarthritic Chondrocytes," *Rheumatology* 41:1413-1418.

Jefferis, R. et al. (1997). "Glycosylation of Antibody Molecules: Structural and Functional Significance," *Chem. Immunol.* 65:111-128.

Johnson, K.S. et al. (1993). "Human Antibody Engineering," *Current Opinion in Structural Biology* 3:564-571.

Jolly, D. (1994). "Viral Vector Systems for Gene Therapy," *Cancer Gene Therapy* 1(1):51-64.

Jones, P.T. et al. (1986). "Replacing the Complementarity-Determinign Regions in a Human Antibody with Those from a Mouse," *Nature* 321:522-525.

Kabat, E.A. et al. (1991). *Sequences of Proteins of Immunological Interest*, Fifth Edition, National Institutes of Health: Bethesda, MD pp. iii-xi (Table of Contents Only.).

Kaplitt, M.G. et al. (1994). "Long-Term Gene Expression and Phenotypic Correction Using Adeno-Associated Virus Vectors in the Mammalian Brain," *Nature Genetics* 8:148-153.

Karlsson, R. et al. (1994). "Kinetic and Concentration Analysis Using BIA Technology," *Methods: A Companion to Methods in Enzymology* Academic Press, Inc. 6:99-110.

Kassel, O. et al. (2001). "Local Increase in the Number of Mast Cells and Expression of Nerve Growth Factor in the Bronchus of Asthmatic Patients After Repeated Inhalation of Allergen at Low-Dose," *Clin. Exp. Allergy* 31:1432-1440.

Katz, J. et al. (1999). "Measurment of Pain," *Surg. Clin. North Am.* 79(2):231-252.

Kawamoto, K. et al. (2002). "Nerve Growth Factor Activates Mast Cells Through the Collaborative Interaction with Lysophosphatidylserine Expressed on the Membrane Surface of Activated Platelets," *J. Immunol.* 168:6412-6419.

Kerr, B.J. et al. (2001). "A Role For the TTX-Resistant Sodium Channel Nav 1.8 in NGF-Induced Hyperalgesia, But Not Neuropathic Pain," *Neuroreport* 12(14):3077-3078.

Kim, J-K. et al. (1994). "Localization of the Site of the Murine IgG1 Molecule that is Involved in Binding to the Murine Intestinal Fc Receptor," *Eur. J. Immunol.* 24:2429-2434.

Kimura, O. et al. (1994). "Retroviral Delivery of DNA into the Livers of Transgenic Mice Bearing Premalignant and Maligant Hepatocellular Carcinomas," *Human Gene Therapy* 5:845-852.

Klein, R. et al. (1990). "The *trk*B Tyrosine Protein Kinase Gene Codes for a Second Neurogenic Receptor That Lacks the Catalytic Kinase Domain," *Cell* 61:647-656.

Knüsel, B. et al. (1991). "K-252b Is a Selective and Nontoxic Inhibitor of Nerve Growth Factor Action on Culutred Brain Neurons," *J. Neurochemistry* 57:955-962.

Knüsel, B. et al. (1992). "K-252b Selectively Potentiates Cellular Actions and *trk* Tyrosine Phosphorylation Mediated by Neurotrophin-3," *J. Neurochemistry* 59:715-722.

Kohler, B. et al. (1975). "Continuous Cultures of Fused Cells Secreting Antibody of Predefined Specificity," *Nature* 256:495-497.

Koizumi, S. et al. (1988). "K-252a: A Specific Inhibitor of the Action of Nerve Growth Factor of PC12 Cells," *J. Neuroscience* 8(2):715-721.

Kuzuna, S. et al. (1975). "Evaluation of Analgesic Agents in Rats with Adjuvant Arthritis," *Chem Pharm. Bull.* 23:1184-1191.

Lamballe, F. et al. (1993). "*trkC* Encodes Multiple Neurotrophin-3 Receptors with Distinct Biological Properties and Substrate Specificities," *EMBO J.* 12(8):3083-3094.

Lambiase, A. et al. (2003). "Clinical Application of Nerve Growth Factor on Human Corneal Ulcer," *Arch. Ital. Biol.* 141:141-148.

Leon, A. et al. (1994). "Mast Cells Synthesize, Store, and Release Nerve Growth Factor," *Proc. Natl. Acad. Sci. USA* 91:3739-3743.

Levi-Montalcini, R. et al. (1968). "Nerve Growth Factor," *Physiol. Rev.* 48(3):534-569.

Lewin, G.R. et al. (1994). "Peripheral and Central Mechanisms of NGF-Induced Hyperalgesia," *European Journal of Neuroscience* 6:1903-1912.

Li, Y-X. et al. (1998). "Expression of a Dominant Negative TrkB Receptor, T1, Reveals a Requirement For Presynaptic Signaling in BDNF-Induced Synaptic Potentiation in Cultured Hippocampal Neurons," *Proc. Natl. Acad. Sci. USA* 95:10884-10889.

Lindhom, D. et al. (1990). "Glucocorticoid Hormones Negatively Regulate Nerve Growth Factor Expression In Vivo and In Cultured Rat Fibroblasts," *Eur. J. Neurosci.* 2:795-801.

Lindsay, R.M. (1988)."Nerve Growth Factors (NGF, BDNF) Enhance Axonal Regeneration But Are Not Required For Survival of Adult Sensory Neurons," *J. Neurosci.* 8(7):2394-2405.

Lindsay, R.M. et al. (1989). "Nerve Growth Factor Regulates Expression of Neuropeptide Genes in Adult Sensory Neurons," *Nature* 337:362-364.

Liu, Z.Z. et al. (1997). "Critical Role of TrkB and Brain-Derived Neurotrophic Factor in the Differentiation and Survival of Retinal Pigment Epithelium," *J. Neurosci.* 17(22):8749-8755.

Lobuglio, A.F. et al. (1989). "Mouse/Human Chimeric Monoclonal Antibody in Man: Kinetics and Immune Response," *Proc. Natl. Acad. Sci. USA* 86:4220-4224.

Lonberg, N. et al. (1995). "Human Antibodies From Transgenic Mice," *Int. Rev. Immunol.* 13:65-93.

Mahato, R.I. et al. (1997). "Cationic Lipid-Based Gene Delivery Systems: Pharmaceutical Perspectives," *Pharm Res.* 14(7):853-859.

Manni, L. et al. (1998). "Role of IL-1β and TNF-α in the Regualtion of NGF in Experimentally Induced Arthritis in Mice," *Rheumatol. Int.* 18:97-102.

Marks, J.D. et al. (1991). "By-Passing Immunication: Human Antibodies From V-Gene Libraries Displayed on Phage," *J. Mol. Biol.* 222:581-597.

Marks, J.D. et al. (1992). "By-Passing Immunization: Building High Affinity Human Antibodies by Chain Shuffling," *Bio/Technol.* 10:779-783.

Matsuda, H. et al. (1988). "Nerve Growth Factor Promotes Human Hemopoietic Colony Growth and Differentiation," *Proc. Natl. Acad. Sci. USA* 85:6508-6512.

Matsuda, H. et al. (1998). "Role of Nerve Growth Factor in Cutaneous Wound Healing: Accelerating Effects in Normal and Healing-Impaired Diabetic Mice," *J. Exp. Med.* 187(3):297-330.

McCafferty, J. et al. (1990). "Phage Antibodies, Filamentous Phage Displaying Antibody Varible Domains," *Nature* 348:552-553.

Meenan, R.F. et al. (1982). "The Arthritis Impact Measurement Scales," *Arthritis and Rheumatism* 25(9):1048-1053.

Michael, G.J. et al. (1997). "Nerve Growth Factor Treatment Increases Brain-Derived Neurotrophic Factor Selectively in TrkA-Expressing Dorsal Root Ganglion Cells and in Their Central Terminations Within the Spinal Cord," *J. Neurosci* 17(21):8476-8490.

Miletic, G. et al. (2002). "Increases in the Concentration of Brain Derived Neurotrophic Factor in the Lumbar Spinal Dorsal Horn are Associated with Pain Behavior Following Chronic Constriction Injury in Rats," *Neurosci Lett.* 319:137-140.

Milstein, C. et al. (1983). "Hybrid Hydridomas and Their Use in Immunohistochemistry," *Nature* 305:537-539.

Møiniche, S. et al. (1997). "Time Course of Subjective Pain Ratings, and Wound and Leg Tenderness After Hysterectomy," *Acta Anaesthesiol. Scand.* 41:785-789.

Møiniche, S. et al. (2002). "A Qualitative and Quantitative Systematic Review of Preemptive Analgesia for Postoperative Pain Relief," *Anesthesiology* 96:725-741.

Morrison, S.L. et al. (1984). "Chimeric Human Antibody Molecules: Mouse Antigen-Binding Domains with Human Constant Region Domains," *Proc. Natl. Acad. Sci* 81:6851-6855.

Myers, E.W. et al. (1988). "Optical Alignments in Linear Space," *CABIOS* 4(1):11-17.

Okragly, A.J. et al. (1991). "Elevated Tryptase, Nerve Growth Factor, Neurotrophin-3 and Glial Cell Line-Derived Neurotrophic Factor Levels In the Urine of Interstitial Cystitis and Bladder Cancer Patients," *J. Urology* 161:438-442.

Otten, U. et al. (1984). "Nerve Growth Factor Induces Plasma Extravasation in Rat Skin," *Eur. J. Pharmacol.* 106:199-201.

Otten, U. et al. (1989). "Nerve Growth Factor Induces Growth and Differentiation of Human B Lymphocytes," *Proc. Natl. Acad. Sci. USA* 86:10059-10063.

Paulus, H.E. et al. (1990). "Anlaysis of Improvement in Individual Rheumatoid Arthritis Patients Treated with Disease-Modifiying Antirheumatic Drugs, Based on the Findings in Patients Treated with Placebo," *Arthritis and Rheumatism* 33(4):477-484.

Pearce, F.L. et al. (1986). "Some Characteristics of Histamine Secretion From Rat Peritoneal Mast Cells Stimulated with Nerve Growth Factor," *J. Physiol.* 372:379-393.

Pearson, C.M. et al. (1959). "Studies of Polyarthritis and Other Lesions Induced in Rats by Injection of Mycobacterial Adjuvant. I. General Clinical and Pathological Characteristics and Some Modifying Factors," *Arthritis Rheum.* 2:440-459.

Peeters, K. et al. (2001). "Production of Antibodies and Antibody Fragments in Plants," *Vaccine* 19:2756-2761.

Petersen, M. et al. (1998). "Nerve Growth Factor Regulates the Expression of Bradykinin Binding Sites on Adult Sensory Neurons Via the Neurotrophin Receptor p. 75," *Neuroscience* 83(1):161-168.

Petty, B.G. et al. (1994). "The Effect of Systemically Administered Recombinant Human Nerve Growth Factor in Healthy Human Subjects," *Annals Neurol.* 36:244-246.

Philip, R. et al. (1994). "Efficient and Sustained Gene Expression in Primary T Lymphocytes and Primary and Cultured Tumor Cells Mediated by Adeno-Associated Virus Plasmid DNA Complexed to Cationic Liposomes," *Mol. Cell Biol.* 14(4):2411-2418.

Pogatzki, E.M. et al. (2002). "Characterization of Aδ- and C-Fibers Innervating the Plantar Rat Hindpaw One Day After an Incision," *J. Neurophysiol.* 87:721-731.

Pogatzki, E.M. et al. (2002). "Role of Rostral Medial Medulla in the Development of Primary and Secondary Hyperalgesia After Incision in the Rat," *Anesthesiology* 96:1153-1160.

Poljak, R. J. et al. (1994). "Production and Structure of Diabodies," *Structure* 2:1121-1123.

Pollock, D.P. et al. (1999). "Transgenic Milk as a Method For the Production of Recombinant Antibodies," *J. Immunol. Methods* 231:147-157.

Pons, J. et al. (1999). "Energetic Analysis of an Antigen/Antibody Interface: Alanine Scanning Mutagenesis and Double Mutant Cycles on the HyHEL-10/Lysozyme Interaction," *Prot. Sci.* 8:958-968.

Prodromou, C. et al. (1992). "Recursive PCR: A Novel Technique for Total Gene Synthesis," *Protein Eng.* 5(8):827-829.

Ravetch, J.V. et al. (1991). "Fc Receptors," *Ann. Rev. Immunol.* 9:457-492.

Raychaudhuri, S.P. et al. (1998). "Psoriatic Keratinocytes Express High Levels of Nerve Growth Factor," *Acta Derm Venereol.* 78:84-86.

Riechmann, L. et al. (1988). "Reshaping Human Antibodies for Therapy," *Nature* 332:323-327.

Ro, L-S. et al. (1999). "Effect of NGF and Anti-NGF on Neuropathic Pain in Rats Following Chronic Constriction Injury of the Sciatic Nerve," *Pain* 79:265-274.

Robinson, D.F. (1971). "Comparison of Labeled Trees with Valency Three," *J. Comb. Theor.* 11:105-119.

Rossi, J.J. et al. eds. (1999). *Intracellular Ribozyme Applications: Principles and Protocols* Horizon Scientific Press: Duarte, CA pp. iii-iv (Table of Contents Only).

Roubenoff, R. et al. (1994). "Rheumatoid Cachexia: Cytokine-Drive Hypermetabolism Accompanying Reduced Body Cell Mass in Chronic Inflammation," *J. Clin. Invest.* 93(6):2379-2386.

Roubenoff, R. et al. (1997). "Adjuvant Arthritis as a Model of Inflammatory Cachexia," *Arthritis Rheum.* 40(3):534-539.

Ruberti, F. et al. (1993). "Cloning and Expression of an Anti-Nerve Growth Factor (NGF) Antibody for Studies Using the Neuroantibody Approach," *Cell. Molec. Neurobiol.* 13(5):559-568.

Saitou, N. et al. (1987). "The Neighbor-Joinging Method: A New Method for Reconstructing Phylogenetic Tree," *Mol. Biol. Evol.* 4(4):406-425.

Schwartz, F. et al. (2002). "Effect of Helium/Neon Laser Irradiation on Nerve Growth Factor Synthesis and Secretion in Skeletal Muscle Cultures," *J. Photochem Photobiol. B: Biology* 66:195-200.

Sevarino, K.A. et al. (1988). "Biosynthesis of Thyrotropin-Releasing Hormone by a Rat Medullary Thyroid Carcinoma Cell Line," *J. Biol. Chem.* 263:620-623.

Shaw, D.R. et al. (1987). "Characterization of a Mouse/Human Chimeric Monoclonal Antibody (17-1A) To A Colon Cancer Tumor-Associated Antigen," *J. Immunol.* 138(12):4534-4538.

Sheets, M.D. et al. (1998). "Efficient Construction of a Large Nonimmune Phage Antibody Library: The Production of High-Affinity Human Single-Chain Antibodies to Protein Antigens," *Proc. Natl. Acad. Sci. USA* 95:6157-6162.

Smyene, R.J. et al. (1994). "Severe Sensory and Sympathetic Neuropathies in Mice Carrying a Disrupted Trk/NGF Receptor Gene," *Nature* 368:246-249.

Sneath, P.H.A. et al. (1973). *Numerical Taxonomy the Principles and Practice of Numerical Taxonomy* W.H. Freeman Press: San Francisco, CA. pp. vii-ix (Table of Contents Only.).

Steiner, P. et al. (1991). "Interleukin-1β and Tumor Necrosis Factor-α Synergistically Stimulate Nerve Growth Factor Synthesis in Rat Mesangial Cells," *Am. J. Physiol.* 261:F792-F798.

Taglialatela, G. et al. (1996). "Suppression of p140$^{trkA}$ Does Not Abolish Nerve Growth Factor-Mediated Rescue of Serum-Free PC12 Cells," J. Neurochem. 66(5):1826-1835.

Thompson, S.W.N. et al. (1995). "Nerve Growth Factor Induces Mechanical Allodynia Associated with Novel A Fibre-Evoked Spinal Reflex Activity and Enhanced Neurokinin-1 Receptor Activation in the Rat," *Pain* 62:219-231.

Thompson, S.W.N. et al. (1999). "Brain-Derived Neurotrophic Factor is an Endogenous Modulator of Nociceptive Responses in the Spinal Cord," *Proc. Natl. Acad. Sci USA* 96(14):7714-7718.

Torcia, M. et al. (1996). "Nerve Growth Facor Is an Autocrine Survival Factor for Memory B Lymphocytes," *Cell* 85:345-356.

Tsoulfas, P. et al. (1993). "The Rat *trkC* Locus Encodes Multiple Neurogenic Receptors That Exhibit Differential Response to Neurotrophin-3 in PC12 Cells," *Neuron* 10:975-990.

Ueyama, T. et al. (1993). "Production of Nerve Growth Factor by Cultured Vascular Smooth Muscle Cells From Spontaneously Hypertensive and Wistar-Kyoto Rats," *J. Hypertens.* 11:1061-1065.

Ullrich, A. et al. (1983). "Human β-Nerve Growth Factor Gene Sequence Highly Homologous to That of Mouse," *Nature* 303:821-825.

Umana, P. et al. (1999). "Engineered Glycoforms of an Antineuroblastoma IgG1 with Optimized Antibody-Dependent Cellular Cytotoxic Activity," *Mature Biotech.* 17:176-180.

Urfer, R. et al. (1997). "Specificity Determinants in Neurotrophin-3 and Design of Nerve Growth Factor-Based trkC Agonists by Changing Central β-Strand Bundle Residues to Their Neurotrophin-3 Analogs," *Biochem.* 36:4775-4781.

Valenzuela, D.M. et al. (1993). "Alternative Forms of Rat TrkC With Different Functional Capabilities," *Neuron* 10:963-974.

Vaughan, T.J. et al. (1996). "Human Antibodies with Sub-Nanomolar Affinities Isolated from a Large Non-Immunized Phage Display Library," *Nature Biotechnology* 14:309-314.

Verhoeyen, M. et al. (1988). "Reshaping Human Antibodies: Grafting an Antilysozyme Activity," *Science* 239:1534-1536.

Waterhouse, P. et al. (1993). "Combinatorial Infection and in vivo Recombination: A Strategy for Making Large Phage Antibody Repertoires," *Nucl. Acids Res.* 21(9):2265-2266.

Wilbur, W.J. et al. (1983). "Rapid Similarity Searches of Nucleic Acid and Protein Data Banks," *Proc. Natl. Acad. Sci. USA* 80:726-730.

Winter, G. et al. (1991). "Man-Made Antibodies," *Nature* 349:293-299.

Winter, G. et al. (1994). "Making Antibodies by Phage Display Technology," *Annu. Rev. Immunol.* 12:433-455.

Wittwer, A.J. et al. (1990). "Glycosylation at Asn-184 Inhibits the Conversion of Single-Chain to Two-Chain Tissue-Type Plasminogen Activator by Plasmin," *Biochem.* 29:4175-4180.

Woffendin, C. et al. (1994). "Nonviral and Viral Delivery of a Human Immunodeficiency Virus Protective Gene into Primary Human T Cells," *Proc. Natl. Acad. Sci. USA* 91:11581-11585.

Woolf, C.J. et al. (1996). "Peripheral Cell Types Contributing to the Hyperalgesic Action of Nerve Growth Factor in Inflammation," *J. Neurosci.* 16(8):2716-2723.

Woolf, N.J. et al. (2001). "Elevation of Nerve Growth Factor and Antisense Knockdown of TrkA Receptor during Contextual Memory Consolidation," *J. Neurosci.* 21(3):1047-1055.

Wright, A. et al. (1997). "Effect of Glycosylation on Antibody Function: Implications for Genetic Engineering," *TibTECH* 15:26-32.

Wu, C.H. et al. (1989). "Targeting Genes: Delivery and Persistent Expression of a Foreign Gene Driven by Mammalian Regulatory Elements in Vivo," *J. Biol. Chem.* 264:16985-16987.

Wu, G.Y. et al. (1991). "Receptor-Mediated Gene Delivery in Vivo: Partial Correction of Genetic Analbuminemia in Nagase Rats," *J. Biol. Chem.* 266(22):14338-14342.

Wu, G.Y. et al. (1994). "Incorporation of Adenovirus into a Ligand-Based DNA Carrier System Results in Retention of Original Receptor Specificity and Enhances Targeted Gene Expression," *J. Biol. Chem.* 269(15):11542-11546.

Wyss, D.F. et al. (1996). "The Structural Role of Sugars in Glycoproteins," *Current Opin. Biotech* 7:409-416.

Yamamoto, T. et al. (2001). "Spinal *N*-acetyl-α-linked Acidic Dipeptidase (NAALASase) Inhibition Attenuates Mechanical Allodynia Induced by Paw Carrageenan Injection in the Rat," *Brain Res.* 909:138-144.

Yan, Q. et al. (1991). "Hypotension Induced by Intravascular Administration of Nerve Growth Factor in the Rat," *Clin. Sci.* 80:565-569.

Zenke, M. et al. (1990). "Receptor-Mediated Endocytosis of Transferrin-Polycation Conjugates: An Efficient Way to Introduce DNA Into Hematopoietic Cells," *Proc. Natl. Acad. Sci. USA* 87:3655-3659.

Zola, H. (1987). "Using Monoclonal Antibodies: Soluble Antigens" Chapter 6 *In Monocolonal Antibodies: A Manual of Techniques* CRC Press, Inc. pp. 147-158.

Baik, R.K. et al. (Nov. 12, 2003). "Anti-NGF Treatment Attenuates Spontaneous Pain and Thermal, but Not Mechanical Hyperalgesia, After Hind Paw Incision in the Rat," *Society for Neuroscience*, Program No. 909.12, one page, Abstract Only.

Abbadie, C. et al. (Jun. 24, 2003). "Impaired Neuropathic Pain Responses in Mice Lacking the Chemokine Receptor CCR2," *Proc. Natl. Acad. Sci. USA* 100(13):7947-7952.

Aloe, L. et al. (1993). "The Synovium of Transgenic Arthritic Mice Expressing Human Tumor Necrosis Factor Contains a High Level of Nerve Growth Factor," *Growth Factors* 9(2):149-155.

Aloe, L. et al. (Sep.-Oct. 1999). "Nerve Growth Factor in the Synovia of Patients with Rheumatoid Arthritis: Correlation with TNF-α and IL-1β and Possible Functional Significance," *Clin. Exp. Rheumatol.* 17(5):632-633.

Altschul, S.F. et al. (1997). "Gapped BLAST and PS1-BLAST: A New Generation of Protein Database Search Programs," *Nucleic Acids Res.* 25(17):3389-3402.

American Chemical Society (1987-1991). *Chemical Abstracts, 12th Collective Index, Chemical Substances*, vols. 106-115, p. 34237CS, col. 3, lines 5-7.

American Chemical Society (1987-1991). *Chemical Abstracts, 12th Collective Index, Chemical Substances*, vols. 106-115, p. 34237CS, col. 3, lines 55-60.

American Chemical Society (1987-1991). *Chemical Abstracts, 12th Collective Index, Chemical Substances*, vols. 106-115, p. 34237CS, col. 3, lines 66-69.

American Chemical Society (1987-1991). *Chemical Abstracts, 12th Collective Index, Chemical Substances*, vols. 106-115, p. 34238CS, col. 1, lines 41-44.

American Chemical Society (1987-1991). *Chemical Abstracts, 12th Collective Index, Chemical Substances*, vols. 106-115, p. 34238CS, col. 2, lines 25-27.

American Chemical Society (1987-1991). *Chemical Abstracts, 12th Collective Index, Chemical Substances*, vols. 106-115, p. 34238CS, col. 2, lines 32-33.

American Chemical Society (1987-1991). *Chemical Abstracts, 12th Collective Index, Chemical Substances*, vols. 106-115, p. 34239CS, col. 3, lines 48-50.

American Chemical Society (1987-1991). *Chemical Abstracts, 12th Collective Index, Chemical Substances*, vols. 106-115, p. 34239CS, col. 3, lines 52-53.

Barbas III, C.F. et al. (Apr. 1994). "In vitro Evolution of a Neutralizing Human Antibody to Human Immunodeficiency Virus Type 1 to Enhance Affinity and Broaden Strain Cross-Reactivity," *Proc. Natl. Acad. Sci. USA* 91:3809-3813.

Barbas III, C.F. et al. (2001). "Vector pComb3X, Figure 2.2" In "Phage-Display Vectors" Chapter 2 *In Phage Display: A Laboratory Manual*, Cold Spring Harbor Laboratory Press: Cold Spring Harbor, NY, pp. 2.9-2.13.

Bellamy, N. (May 1989). "Pain Assessment in Osteoarthritis: Experience With the WOMAC Osteoarthritis Index," *Semin. Arthritis Rheum.* 18(4 Suppl. 2):14-17.

Bellamy, N. et al. (Dec. 1988). "Validation Study of WOMAC: A Health Status Instrument for Measuring Clinically Important Patient Relevant Outcomes to Antirheumatic Drug Therapy in Patients with Osteoarthritis of the Hip or Knee," *J. Rheumatol.* 15(12):1833-1840.

Bibel, M. et al. (Dec. 1, 2000). "Neurotrophins: Key Regulators of Cell Fate and Cell Shape in the Vertebrate Nervous System," *Genes Dev.* 14(23):2919-2937.

Brosseau, L. et al. (2003). "Thermotherapy for Treatment of Osteoarthritis," *The Cochrane Database of Systematic Reviews* Issue 4, Art No. CD004522, pp. 1-20.

Chaplan, S.R. et al. (1994). "Quantitative Assessment of Tactile Allodynia in the Rat Paw," *J. Neuroscience Methods* 53:55-63.

Chen, Y. et al. (Nov. 5, 1999). "Selection and Analysis of an Optimized Anti-VEGF Antibody: Crystal Structure of an Affinity-Matured Fab in Complex with Antigen," *J. Mol. Biol.* 293(4):865-881.

Choi, S-S. et al. (2003). "Antinociceptive Mechanisms of Orally Administered Decursinol in the Mouse," *Life Sciences* 73(4):471-485.

Clohisy, D.R. et al. (2003). "Skeletal Complications of Malignancy: Bone Cancer Pain," *Clinical Orthopaedics and Related Research* 415S:S279-S288.

Corey, E. et al. (Jun. 1, 2002). "Establishment and Characterization of Osseous Prostate Cancer Models: Intra-Tibial Injection of Human Prostate Cancer Cells," *Prostate* 52(1):20-33.

Dicou, E. et al. (1996). "Nerve Growth Factor (NGF) Autoantibodies and NGF in the Synovial Fluid: Implications in Spondylarthropathies," *Autoimmunity* 24(1):1-9.

Dicou, E. et al. (Dec. 13, 1993). "Increased Frequency of NGF in sera of Rheumatoid Arthritis and Systemic Lupus Erythematosus Patients," *NeuroReport* 5(3):321-324.

Dicou, E. et al. (Jan. 1994). "Natural Autoantibodies Against the Nerve Growth Factor in Autoimmune Diseases," *J. Neuroimmunol.* 49(1):224 (Erratum).

Dicou, E. et al. (May 1997). "Evidence That Natural Autoantibodies Against the Nerve Growth Factor (NGF) May Be Potential Carriers of NGF," *J. Neuroimmunol.* 75:200-203.

Dicou, E. et al. (Sep. 1993). "Natural Autoantibodies Against the Nerve Growth Factor in Autoimmune Diseases," *J. Neuroimmunol.* 47(2):159-167.

Edoff, K. et al. (Feb. 2000). "Retrograde Tracing and Neuropeptide Immunohistochemistry of Sensory Neurones Projecting to the Cartilaginous Distal Femoral Epiphysis of Young Rats," *Cell & Tissue Research* 299(2):193-200.

Fawcett, D.W. (1986). "Bone" Chapter 8 *In A Textbook of Histology*, Dreibelbis, D. ed., Eleventh Edition, W.B. Saunders Co.: Philadelphia, PA, pp. 211-216 and Table of Contents pp. v-xi.

Fischer, H.P. et al. (Jun. 1998). "A Possible Role for Saliva as Diagnostic Fluid in Patients with Chronic Pain," *Semin. Arthritis Rheum.* 27(6):348-359.

Fjell, J. et al. (Feb. 1999). "In Vivo NGF Deprivation Reduces SNS Expression and TTX-R Sodium Currents in IB4-Negative DRG Neurons," *J. Neurophysiol.* 81(2):803-810.

Garcia-Castellano, J.M. et al. (2000). "Is Bone a Target-Tissue for the Nervous System? New Advances on the Understanding of Their Interactions," *Iowa Orthop. J.* 20:49-58.

Garrett, N.E. et al. (Jul. 11, 1997). "Effect of Capsaicin on Substance P and Nerve Growth Factor in Adjuvant Arthritic Rats," *Neurosci. Lett.* 230:5-8.

Gavilondo, J.V. et al. (Jul. 2000). "Antibody Engineering at the Millennium," *BioTechniques* 29:128-145.

GenBank Accession No. CAA09181, created Dec. 2, 1998, Patterson et al.

GenBank Accession No. P01859, created Jul. 21, 1986, Ellison et al.

Greene, L.A. et al. (Jul. 1976). "Establishment of a Noradrenergic Clonal Line of Rat Adrenal Pheochromocytoma Cells Which Respond to Nerve Growth Factor," *Proc. Nat. Acad. Sci. USA* 73(7):2424-2428.

Halliday, D.A. et al. (Jun. 1998). "Elevated Nerve Growth Factor Levels in the Synovial Fluid of Patients With Inflammatory Joint Disease," *Neurochem. Res.* 23(6):919-922.

Hasselström, J. et al. (Jul. 1996). "Disposition and Analgesic Effects of Systemic Morphine, Morphine-6-glucuronide and Normorphine in Rat," *Pharmacology & Toxicology* 79(1):40-46.

Haynes, M.K. et al. (Dec. 2002). "Phenotypic Characterization of Inflammatory Cells From Osteoarthritic Synovium and Synovial Fluids," *Clin. Immunol.* 105(3):315-325.

Hill, R (Jul. 2000). "$NK_1$ (Substance P) Receptor Antagonists—Why Are They Not Analgesic in Humans?" *Trends Pharmacol. Sci.* 21(7):244-246.

Honoré, et al. (2000). "Cellular and Neurochemical Remodeling of the Spinal Cord in Bone Cancer Pain," *Prog. Brain Res.* 129:389-397.

Honoré, P. et al. (May 2000). "Osteoprotegerin Blocks Bone Cancer-Induced Skeletal Destruction, Skeletal Pain and Pain-Related Neurochemical Reorganization of the Spinal Cord," *Nat. Med.* 6(5):521-528.

Honoré, et al. (Jun. 23, 2000). "Murine Models of Inflammatory, Neuropathic and Cancer Pain Each Generates a Unique Set of Neurochemical Changes in the Spinal Cord and Sensory Neurons," *Neuroscience* 98(3):585-598.

Huang, E.J. et al. (2001). "Neurotrophins: Roles in Neuronal Development and Function," *Annu. Rev. Neurosci.* 24:677-736.

Hunt, S.P. et al. (Aug. 13, 1987). "Induction of c-*fos*-like Protein in Spinal Cord Neurons Following Sensory Stimulation," *Nature* 328:632-634.

Huse, W.D. et al. (1993). "Increased Antibody Affinity and Specificity by Codon-Based Mutagenesis," *Intern. Rev. Immunol.* 10:129-137.

Iadarola, M.J. et al. (1988). "Differential Activation of Spinal Cord Dynorphin and Enkephalin Neurons During Hyperalgesia: Evidence Using cDNA Hybridization," *Brain Res.* 455(2):205-212.

International Search Report for PCT Application No. PCT/US03/32113, filed Oct. 8, 2003, mailed Apr. 10, 2006, four pages.

International Search Report for PCT Application No. PCT/US04/05162 filed Feb. 19, 2004, mailed Mar. 28, 2006, four pages.

International Search Report for PCT Application No. PCT/US2005/011786, filed Jul. 4, 2005, mailed Feb. 20, 2006, five pages.

Jongen, J.L.M. et al. (2002). "Neurotrophic Factors and Cancer Pain: The Expression of NGF, GDNF and BDNF by the Murine Osteolytic Sarcoma Cell Line 2472 in vitro and in vivo and Their Potential Involvement in Bone Cancer Pain," *32nd Annual Meeting of the Society for Neuroscience*, Orlando, FL, (Nov. 2-7, 2002), Abstract 52.2, located at <http://sfn.scholarone.com/iten2002/main.html>, last visited Mar. 2, 2006, two pages.

Kasai, M. et al. (1999). "Endogenous Nerve Growth Factor Increases the Sensitivity to Bradykinin in Small Dorsal Root Ganglion Neurons of Adjuvant Inflamed Rats," *Neuroscience Letters* 272(1):41-44.

Kazemier, B. et al. (1996). "Determination of Active Single Chain Antibody Concentrations in Crude Periplasmic Fractions," *J. Immunol. Methods* 194(2):201-209.

Lewin, G.R. et al. (May 1993). "Nerve Growth Factor-Induced Hyperalgesia in the Neonatal and Adult Rat," *J. Neurosci.* 13(5):2136-2148.

Luger, N.M. et al. (May 15, 2001). "Osteoprotegerin Diminishes Advanced Bone Cancer Pain," *Cancer Res.* 61:4038-4047.

Luger, N.M. et al. (2002). "Efficacy of Systemic Morphine Suggests a Fundamental Difference in the Mechanisms that Generate Bone Cancer vs. Inflammatory Pain," *Pain* 99:397-406.

Mach, D.B. et al. (2002). "Origins of Skeletal Pain: Sensory and Sympathetic Innervation of the Mouse Femur," *Neuroscience* 113(1):155-166.

Mantyh, P.W. et al. (Mar. 2002). "Molecular Mechanisms of Cancer Pain," *Nature Reviews Cancer* 2(3):201-209.

McCarthy, B.G. et al. (Oct. 1995). "Cutaneous Innervation in Sensory Neuropathies," *Neurology* 45:1848-1855.

McDonald, N.Q. et al. (Dec. 5, 1991). "New Protein Fold Revealed by a 2.3-Å Resolution Crystal Structure of Nerve Growth Factor," *Nature* 354:411.

McMahon, S.B. (Mar. 29, 1996). "NGF as a Mediator of Inflammatory Pain," *Phil. Trans. R. Soc. Land. B* 351(1338):431-440.

Molander, C. et al. (1987). "Spinal Cord Projections From Hindlimb Muscle Nerves in the Rat Studied by Transganglionic Transport of Horseradish Peroxidase, Wheat Germ Agglutinin Conjugated Horseradish Peroxidase, or Horseradish Peroxidase With Dimethylsulfoxide," *J. Comp. Neurol.* 260:246-255.

Muller, Y.A. et al. (1998). "VEGF and the Fab Fragment of a Humanized Neutralizing Antibody: Crystal Structure of the Complex at 2.4 Å Resolution and Mutational Analysis of the Interface," *Structure* 6(9):1153-1167.

Myers, R.R. et al. (Sep. 1996). "Reduced Hyperalgesia in Nerve-Injured WLD Mice: Relationship to Nerve Fiber Phagocytosis, Axonal Degeneration, and Regeneration in Normal Mice," *Exp. Neurol.* 141(1):94-101.

Niissalo, S. et al. (Jun. 2002). "Neuropeptides in Experimental and Degenerative Arthritis," *Ann. N.Y. Acad. Sci.* 966:384-399.

Noguchi, K. et al. (1991). "Dynorphin Expression and Fos-like Immunoreactivity Following Inflammation Induced Hyperalgesia are Colocalized in Spinal Cord Neurons," *Molecular Brain Research* 10(3):227-233.

Peter, E.A. et al. (Oct. 30, 2001). "Ibuprofen Versus Acetaminophen with Codeine for the Relief of Perineal Pain after Childbirth: A Randomized Controlled Trial," *CMAJ* 165(9):1203-1209.

Pezet, S. et al. (Feb. 1, 2001). "Differential Regulation of NGF Receptors in Primary Sensory Neurons by Adjuvant-Induced Arthritis in the Rat," *Pain* 90(1-2):113-125.

Pozza, M. et al. (May 2000). "A Histochemical Study of the Rheumatoid Synovium: Focus on Nitric Oxide, Nerve Growth Factor High Affinity Receptor, and Innervation," *J. Rheumatol.* 27(5):1121-1127.

Puigdellivol-Sánchez, A. et al. (1998). "Sciatic and Femoral Nerve Sensory Neurones Occupy Different Regions of the L4 Dorsal Root Ganglion in the Adult Rat," *Neurosci. Lett.* 251(3):169-172.

Puigdellivol-Sánchez, A. et al. (Oct. 1, 2000). "Contribution of Femoral and Proximal Sciatic Nerve Branches to the Sensory Innervation of Hindlimb Digits in the Rat," *The Anatomical Record* 260(2):180-188.

Rader, C. et al. (2001). "Antibody Engineering" Chapter 13 *In Phage Display, A Laboratory Manual*, Barbas III, C.F. et al. eds., Cold Spring Harbor Laboratory Press: Cold Spring Harbor, NY, pp. 13.1-13.15.

Rosok, M.J. et al. (Sep. 13, 1996). "A Combinatorial Library Strategy for the Rapid Humanization of Anticarcinoma BR96 Fab," *The Journal of Biological Chemistry* 271(37):22611-22618.

Rudikoff, S. et al. (Mar. 1982). "Single Amino Acid Substitution Altering Antigen-Binding Specificity," *Proc. Natl. Acad. Sci. USA* 79:1979-1983.

Sabino, M.A.C. et al. (Dec. 15, 2002). "Simultaneous Reduction in Cancer Pain, Bone Destruction, and Tumor Growth by Selective Inhibition of Cyclooxygenase-2," *Cancer Res.* 62:7343-7349.

Sabino, M.A.C. et al. (May 1, 2003). "Different Tumors in Bone Each Give Rise to a Distinct Pattern of Skeletal Destruction, Bone Cancer-Related Pain Behaviors and Neurochemical Changes in the Central Nervous System," *International Journal of Cancer* 104(5):550-558.

Safieh-Garabedian, B. et al. (Aug. 1995). "Contribution of Interleukin-1β to the Inflammation-Induced Increase in Nerve Growth Factor Levels and Inflammatory Hyperalgesia," *Br. J. Pharmacol.* 115(7):1265-1275.

Schwei, M.J. et al. (Dec. 15, 1999). "Neurochemical and Cellular Reorganization of the Spinal Cord in a Murine Model of Bone Cancer Pain," *J. Neuroscience* 19(24):10886-10897.

Shelton, D.L. et al. (Dec. 1984). "Expression of the β-nerve Growth Factor Gene Correlates with the Density of Sympathetic Innervation in Effector Organs," *Proc. Natl. Acad. Sci. USA* 81:7951-7955.

Shelton, D.L. et al. (1995). "Neurotrophins and Neurotrophin Antagonists as Potential Therapeutics," *Restorative Neurology and Neuroscience* 8(1-2):99-100.

Shu, X. et al. (1999). "Nerve Growth Factor Acutely Sensitizes the Response of Adult Rat Sensory Neurons to Capsaicin," *Neurosci. Lett.* 274(3):159-162.

Stedman, T.L. (1982). *Illustrated Stedman's Medical Dictionary*, Williams & Wilkins: Baltimore, MD, 24th Edition, p. 670.

Szekanecz, Z. et al. (Jun. 2000). "Temporal Expression of Inflammatory Cytokines and Chemokines in Rat Adjuvant-Induced Arthritis," *Arthritis & Rheumatism* 43(6):1266-1277.

Tang, Y. et al. (Sep. 24, 1999). "Use of a Peptide Mimotope to Guide the Humanization of MRK-16, and Anti-P-Glycoprotein Monoclonal Antibody," *The Journal of Biological Chemistry* 274(39):27371-27378.

Thompson, J.E. et al. (1999). "A Fully Human Antibody Neutralising Biologically Active Human TGFβ2 for use in Therapy," *J. Immunol. Methods* 227:17-29.

Tofaris, G.K. et al. (Aug. 1, 2002). "Denervated Schwann Cells Attract Macrophages by Secretion of Leukemia Inhibitory Factor (LIF) and Monocyte Chemoattractant Protein-1 in a Process Regulated by Interleukin-6 and LIF," *J. Neurosci.* 22(15):6696-6703.

Tsujino, H. et al. (Feb. 2000). "Activating Transcription Factor 3 (ATF3) Induction by Axotomy in Sensory and Motoneurons: A Novel Neuronal Marker of Nerve Injury," *Molecular & Cellular Neuroscience* 15(2):170-182.

Vajdos, F.F. et al. (2002), "Comprehensive Functional Maps of the Antigen-Binding Site of an Anti-ErbB2 Antibody Obtained with Shotgun Scanning Mutagenesis," *J. Mol. Biol.* 320:415-428.

Vanderah, T.W. et al. (Apr. 2001). "Mechanisms of Opioid-Induced Pain and Antinociceptive Tolerance: Descending Facilitation and Spinal Dynorphin," *Pain* 92(3):5-9.

Vigneti, E. et al. (1993). "Production and Characterization of a Monoclonal Antibody Against Nerve Growth Factor (NGF) Which Recognizes Rodent and Human NGF," *Year Immunol.* 7:146-149.

Villanueva, L. (Dec. 2000). "Is There a Gap Between Preclinical and Clinical Studies of Analgesia?" *Trends Pharmacol. Sci.* 21(12):461-462.

Wiesmann, C. et al. (Sep. 9, 1999). "Crystal Structure of Nerve Growth Factor in Complex with the Ligand-Binding Domain of the TrkA Receptor," *Nature* 401(6749):184-188.

Winter, C.A. et al. (Jun. 1966). "Treatment of Adjuvant Arthritis in Rats with Anti-Inflammatory Drugs," *Arthritis Rheum.* 9(3):394-404.

Woolf, C.J. et al. (1994). "Nerve Growth Factor Contributes to the Generation of Inflammatory Sensory Hypersensitivity," *Neuroscience* 62(2):327-331.

Wu, H. et al. (Nov. 19, 1999). "Humanization of a Murine Monoclonal Antibody by Simultaneous Optimization of Framework and CDR Residues," *J. Mol. Biol.* 294(1):151-162.

Wu, S.M. et al. (1998). "Oxidized $\alpha_2$-Macroglobulin ($\alpha_2$M) Differentially Regulates Receptor Binding by Cytokines/Growth Factors: Implications for Tissue Injury and Repair Mechanisms in Inflammation," *The Journal of Immunology* 161:4356-4365.

Wu, Z. et al. (Dec. 2000). "Immunohistochemical Study of NGF and its Receptors in the Synovial Membrane of the Ankle Joint of Adjuvant-Induced Arthritic Rats," *Histochem. Cell Biol.* 114(6):456-459.

Yelton, D.E. et al. (1995). "Affinity Maturation of the BR96 Anti-Carcinoma Antibody by Codon-Based Mutagenesis," *The Journal of Immunology* 155:1994-2004.

ATCC Search Results for "911 Mab" located at <http://www.atcc.org/common/catalog/wordSearch/results.cfm>, last visited Aug. 30, 2006, one page.

Berzofsky, J.A. et al. (1993). "Immunogenicity and Antigen Structure" Chapter 8 *In Fundamental Immunology*, Paul, W.E. ed., Raven Press: New York, NY, p. 242.

Brennan, T.J. et al. (2005). "Mechanisms of Incisional Pain," *Anesthesiology Clin. N. Am.* 23:1-20.

Cromartie, W.J. et a. (1977). "Arthritis in Rats After Systemic Injection of Streptococcal Cells or Cell Walls," *The Journal of Experimental Medicine* 146:1585-1602.

Honoré, P. et al. (2006). "Interleukin-1αβ Gene-Deficient Mice Show Reduced Nociceptive Sensitivity in Models of Inflammatory and Neuropathic Pain but not Post-Operative Pain," *Behavioural Brain Research* 167:355-364.

Kehlet, H. (Apr. 1995). "Synergism Between Analgesics," *Ann. Med.* 27(2):259-262.

Leem, J.W. et al. (2000). "Anti-NGF Treatment Suppresses Abnormal Pain Behaviors Induced After Spinal Cord Inury in the Rat," *30th Annual Meeting of the Society of Neuroscience*, New Orleans, LA, Nov. 4-9, 2000, *Society for Neuroscience Abstracts* 26(2):1690, Abstract No. 633.1.

Muyldermans, S. (2001). "Single Domain Camel Antibodies: Current Status," *Reviews in Molecular Biotechnology* 74:277-302.

Owolabi, J.B. et al. (1999). "Characterization of Antiallodynic Actions of ALE-0540, a Novel Nerve Growth Factor Receptor Antagonist in the Rat," *J. Pharmacol. Exp. Ther.* 289(3):1271-1276.

Rinat Neurosciences. (Date Unknown). "RN624 A New Approach to Pain Therapy," located at <http://64.233.161.104/search?q=cache:nYXEK1HDbdlJ:www.rinatneuro.com/product/RN6 . . . >, last visited Jul. 5, 2006, five pages.

Sequence Alignments for Sequence Searches of SEQ ID Nos. 1-8, pp. 1-8.

Sunshine, A. et al. (Jul. 1987). "Analgesic Efficacy of Two Ibuprofen-Codeine Combinations for the Treatment of Postepisiotomy and Postoperative Pain," *Clin. Pharmacol. Ther.* 42(1):374-380.

Supplementary European Search Report mailed Sep. 12, 2006, for EP Application No. 03779091.2 filed Oct. 3, 2003, four pages.

Yu, Y.C. et al. (2002). "Two Variables That can be Used as Pain Indices in Experimental Animal Models of Arthritis," *Journal of Neuroscience Methods* 115:107-113.

Zahn, P.K. et al. (Sep.-Oct. 2002). "Mechanisms for Pain Cause by Incisions," *Regional Anesthesia and Pain Medicine* 27(5):514-516.

\* cited by examiner

Proportion of intact wounds after incision and treatment with saline, anti-NGF antibody 911, or ketorolac

METHODS FOR TREATING POST-SURGICAL PAIN BY ADMINISTERING AN ANTI-NERVE GROWTH FACTOR ANTAGONIST ANTIBODY

CROSS-REFERENCE TO RELATED APPLICATIONS

This application claims the priority benefit of provisional application U.S. Ser. No. 60/417,197, filed Oct. 8, 2002, the contents of which is incorporated by reference in its entirety.

STATEMENT REGARDING FEDERALLY SPONSORED RESEARCH OR DEVELOPMENT

This invention was made with U.S. Government support under Contract No. DAAD19-03-C-0006, awarded by the DARPA. The U.S. Government may have certain rights in this invention.

FIELD OF THE INVENTION

The present invention relates to the use of an anti-NGF antagonist antibody for the prevention, amelioration, or treatment of post-surgical pain.

BACKGROUND OF THE INVENTION

Nerve growth factor (NGF) was the first neurotrophin to be identified, and its role in the development and survival of both peripheral and central neurons has been well characterized. NGF has been shown to be a critical survival and maintenance factor in the development of peripheral sympathetic and embryonic sensory neurons and of basal forebrain cholinergic neurons (Smeyne, et al., *Nature* 368:246-249 (1994); Crowley, et al., *Cell* 76:1001-1011 (1994)). NGF upregulates expression of neuropeptides in sensory neurons (Lindsay, et al., *Nature* 337:362-364 (1989)), and its activity is mediated through two different membrane-bound receptors, the TrkA tyrosine kinase receptor and the p75 receptor which is structurally related to other members of the tumor necrosis factor receptor family (Chao, et al., *Science* 232:518-521 (1986)).

In addition to its effects in the nervous system, NGF has been increasingly implicated in processes outside of the nervous system. For example, NGF has been shown to enhance vascular permeability (Otten, et al., *Eur J. Pharmacol.* 106:199-201 (1984)), enhance T- and B-cell immune responses (Otten, et al., *Proc. Natl. Acad. Sci. USA* 86:10059-10063 (1989)), induce lymphocyte differentiation and mast cell proliferation and cause the release of soluble biological signals from mast cells (Matsuda, et al., *Proc. Natl. Acad. Sci. USA* 85:6508-6512 (1988); Pearce, et al., *J. Physiol.* 372:379-393 (1986); Bischoff, et al., *Blood* 79:2662-2669 (1992); Horigome, et al., *J. Biol. Chem.* 268:14881-14887 (1993)). Although exogenously added NGF has been shown to be capable of having all of these effects, it is important to note that it has only rarely been shown that endogenous NGF is important in any of these processes in vivo (Torcia, et al., *Cell.* 85(3):345-56 (1996)). Therefore, it is not clear what the effect might be, if any, of inhibiting the bioactivity of endogenous NGF.

NGF is produced by a number of cell types including mast cells (Leon, et al., *Proc. Natl. Acad. Sci. USA* 91:3739-3743 (1994)), B-lymphocytes (Torcia, et al., *Cell* 85:345-356 (1996)), keratinocytes (Di Marco, et al., *J. Biol. Chem.* 268:22838-22846)), smooth muscle cells (Ueyama, et al., *J. Hypertens.* 11: 1061-1065 (1993)), fibroblasts (Lindholm, et al., *Eur. J. Neurosci.* 2:795-801 (1990)), bronchial epithelial cells (Kassel, et al., *Clin, Exp. Allergy* 31:1432-40 (2001)), renal mesangial cells (Steiner, et al., *Am. J. Physiol.* 261: F792-798 (1991)) and skeletal muscle myotubes (Schwartz, et al., *J Photochem, Photobiol. B* 66:195-200 (2002)). NGF receptors have been found on a variety of cell types outside of the nervous system. For example, TrkA has been found on human monocytes, T- and B-lymphocytes and mast cells.

An association between increased NGF levels and a variety of inflammatory conditions has been observed in human patients as well as in several animal models. These include systemic lupus erythematosus (Bracci-Laudiero, et al., *Neuroreport* 4:563-565 (1993)), multiple sclerosis (Bracci-Laudiero, et al., *Neurosci. Lett.* 147:9-12 (1992)), psoriasis (Raychaudhuri, et al., *Acta Derm. l'enereol.* 78:84-86 (1998)), arthritis (Falcimi, et al., *Ann. Rheum. Dis.* 55:745-748 (1996)), interstitial cystitis (Okragly, et al., *J. Urology* 161:438-441 (1991)) and asthma (Braun, et al., *Eur. J Immunol.* 28:3240-3251 (1998)).

Consistently, an elevated level of NGF in peripheral tissues is associated with inflammation and has been observed in a number of forms of arthritis. The synovium of patients affected by rheumatoid arthritis expresses high levels of NGF while in non-inflamed synovium NGF has been reported to be undetectable (Aloe, et al., *Arch. Rheum.* 35:351-355 (1992)). Similar results were seen in rats with experimentally induced rheumatoid arthritis (Aloe, et al., *Clin. Exp. Rheumatol.* 10:203-204 (1992)). Elevated levels of NGF have been reported in transgenic arthritic mice along with an increase in the number of mast cells. (Aloe, et al., *Int. J. Tissue Reactions—Exp. Clin. Aspects* 15:139-143 (1993)).

Treatment with exogenous NGF leads to an increase in pain and pain sensitivity. This is illustrated by the fact that injection of NGF leads to a significant increase in pain and pain sensitivity in both animal models (Amann, et al., *Pain* 64, 323-329 (1996); Andreev, et al., *Pain* 63, 109-115 (1995)) and human (Dyck, et al., *Neurology* 48, 501-505 (1997); Petty, et al., *Annals Neurol.* 36, 244-246 (1994)). NGF appears to act by multiple mechanisms including inducing the neurotrophin BDNF (Apfel, et al., *Mol. Cell. Neurosci.* 7(2), 134-142 (1996); Michael, et al., *J Neurosci* 17, 8476-8490 (1997)) which in turn changes pain signal processing in the spinal cord (Hains, et al., *Neurosci Lett.* 320(3), 125-8 (2002); Miletic, et al., *Neurosci Lett.* 319(3), 137-40 (2002); Thompson, et al., *Proc Natl Acad Sci USA* 96(14), 7714-8 (1999)), inducing changes in the peripheral and central connections of the sensory neurons and other pain-transmitting neurons in the spinal cord (Lewin, et al., *European Journal of Neuroscience* 6, 1903-1912 (1994); Thompson, et al., *Pain* 62, 219-231 (1995)), inducing changes in axonal growth (Lindsay, R M, *J Neurosci.* 8(7), 2394-405 (1988)) inducing bradykinin receptor expression (Peterson et al., *Neuroscience* 83:161-168 (1998)), inducing changes in expression of genes responsible for nerve activation and conduction such as ion channels (Boettger, et al., *Brain* 125(Pt 2), 252-63 (2002); Kerr, et al., *Neuroreport* 12(14), 3077-8 (2001); Gould, et al., *Brain Res* 854(1-2), 19-29 (2000)), potentiating the pain related receptor VR1 (Chuang, et al., *Nature* 411 (6840), 957-62 (2001); and causing pathological changes in muscles (Foster, et al., *J Pathol* 197(2), 245-55 (2002)). Many of these changes take place directly on the pain transmitting sensory neurons and apparently are not dependent on concomitant inflammation. In addition, there are at least two other cell types known to respond to NGF and that may be involved in changes of pain sensation or sensitivity. The first of these, the mast cell, has been reported to respond to NGF with degranulation (Yan, et al., *Clin. Sci.* (*Lond*) 80:565-569 (1991)) or, in other studies, to cause or increase mediator production or release in collaboration with other agents (Pearce and Thompson, *J. Physiol.* 372:379-393 (1986), Kawamoto, et al., *J. Immunol.* 168:6412-6419 (2002)). It has clearly been shown in the rat that NGF mediated pain responses are at least somewhat mediated by mast cells (Lewin, et al., *Eur. J. Neurosci.* 6:1903-1912 (1994), Woolf, et al., *J. Neurosci.* 16:2716-2723 (1996) although the potential relevance of this remains to be shown in humans. Primary sympathetic neurons are also known to respond to NGF and to also be involved in pain signaling (Aley, et al., *Neuroscience* 71:1083-1090 (1996)). It is clear that removing sympathetic innervation modifies the hyperalgesia normally seen in response to treatment with NGF (Woolf, et al., *J. Neurosci.* 16:2716-2723 (1996)).

Twenty-three million patients have surgical procedures each year. Pain is usually localized within the vicinity of the surgical site. Post-surgical pain can have two clinically important aspects, namely resting pain, or pain that occurs when the patient is not moving and mechanical pain which is exacerbated by movement (coughing/sneezing, getting out of bed, physiotherapy, etc.). The major problem with post-surgical pain management for major surgery is that the drugs currently used have a variety of prominent side effects that delay recovery, prolong hospitalization and subject certain vulnerable patient groups to the risk of serious complications. Post-surgical pain, or pain that occurs after surgery or traumatic injury is a serious and often intractable medical problem.

There are two general categories of medication for the treatment of pain, both of which have disadvantages. The first category includes the nonsteroidal anti-inflammatory drugs (NSAIDs) which are used to treat mild or moderate pain, but whose therapeutic use is limited by undesirable gastrointestinal effects such as gastric erosion, the formation of peptic ulcer or the inflammation of the duodenum and of the colon. NSAIDs also can cause renal toxicity with prolonged use, and further, as described below, are not very effective for treating pain associated with or arising from certain conditions, including post-surgical pain. The second category includes morphine and related opioids which are used to treat moderate to severe pain but whose therapeutic use is limited because of undesirable effects such as sedation, confusion, constipation, respiratory depression, renal colic, tolerance to prolonged use and the risk of addiction. Compounds useful for treating pain with fewer or no side effects are therefore needed.

Pain is often categorized as "inflammatory", "neuropathic" or "visceral", but these traditional general labels have inherent problems. They imply mechanistic similarity or identity among all sources of pain within one of these very general categories. In fact, there are many different types of inflammatory pain and sources of pain that are neither inflammatory nor neuropathic. Further, types of pain that have an inflammatory component, and/or are traditionally termed "inflammatory", does not mean that other physiological aspects do not contribute to the pain state. For example, both osteoarthritis and interstitial cystitis would be defined by their names as sterile inflammatory conditions of respectively joints or the urinary bladder, but it is clear that the pains associated with these two conditions are mechanistically quite different from each other. This is indicated by the varying effects of a given type of anti-pain medication with respect to these types of pain. The majority of patients with osteoarthritis receive good pain relief (at least initially) with NSAIDs. However, NSAIDs treatment is completely ineffective with interstitial cystitis.

Post-surgical pain (interchangeably termed, post-incisional pain) is often considered a variety of inflammatory pain. While there may be an "inflammatory" component to post-surgical pain, clearly additional mechanisms are involved. For example, during surgery or other injury, both vasculature and nerves are cut or torn. This does not happen in a tissue undergoing only inflammation. It is clear that cutting a nerve can induce ongoing activity, which is perceived as painful. In addition, severing blood vessels lead to a tissue that is relatively ischemic, also a painful stimulus that is not present during inflammation alone.

The different mechanisms involved in surgical or injury-induced pain as compared to inflammation is exemplified by the varying pharmacology and underlying anatomical substrates of pain relief in the two conditions. Yamamoto, et al., (*Brian Res.* 909(1-2):138-144 (2001)) have shown that inhibition of spinal N-acetyl-alpha-linked acidic dipeptidase (NAALADase) causes a marked attenuation of mechanical pain which accompanies the inflammatory stimulus of carrageenan injection. However, in parallel experiments where NAALADase was inhibited in an identical fashion after an incision, there was no attenuation of mechanical pain. These observations demonstrate that the biochemistry or pharmacology underlying post-surgical pain is distinct from those underlying inflammatory pain. The anatomical structures important in modulating pain sensation have also been examined in post-surgical and other pain states (Pogatzki, et al., *Anesthesiology*, 96(5):1153-1160 (May 2002)). Descending influences for the brainstem, more specifically the rostral medial medulla, are important modulators of secondary hyperalgesia in general inflammatory, neuropathic and visceral pain states. When the brain stem area was lesioned, no change in any pain response measured after incision was observed. These results indicate that primary and secondary hyperalgesia after an incision are not modulated by descending influence from the RMM. The lack of contribution of descending facilitatory influences from the RMM to secondary hyperalgesia after gastrocnemius incision supports the notion that incision-induced pain involved dissimilar mechanisms compared with inflammatory and neuropathic pain. In addition to the obvious differences in post-surgical or injury-induced pain from inflammatory, visceral or neuropathic pain, these results demonstrate that the mechanisms involved in post-surgical pain (or injury-induced pain) are clearly different from other pains. Further, the utility of a particular pharmacological (or other) intervention in treating post-surgical pain is not predictable by testing that pharmacological agent or intervention in inflammatory, visceral or neuropathic pain models.

Disappearance of pain at rest and persistence of pain with activities and in response to mechanical stimuli at the wound site is also present in patients after surgery. (Moiniche, et al., *Acta Anaesthesiol. Scand.* 41:785-9 (1997)). Studies suggest that pain at rest and evoked pain caused by incisions are likely transmitted by different afferent fiber populations and/or different receptors. Other than using local anesthetics to inhibit these evoked responses, few drugs that markedly reduce pain with coughing and movement after surgery are available.

Pretreatment with a local anesthetic to block the pain during the experimental incision has been shown to initially prevent ongoing pain and the primary mechanical hyperalgesia. Pain from the incisions also disappears when lidocaine is injected after the injury. However, as the local anesthetic effect abates, the primary hyperalgesia returns. In patients, local anesthetic injections made before surgery are roughly equivalent for reducing pain to injections made after surgery. (Moiniche, et al., *Anesthesiology* 96:725-41 (2002))

Clinical studies experiments in human volunteers, and a preclinical incision model agree that administration of local anesthetic before or after the incision are roughly equivalent. The activation of central pain transmitting neurons during incision and sensitization are not necessary for pain behaviors several days later. Rather, for incisions, enhanced responsiveness of central neurons and pain require ongoing afferent input from the incision. After any preincision analgesic treatment abates, the surgical wound appears capable of reinitiating sensitization and regenerating the pain responses. (Pogatzki, et al., *J Neurophysiol* 87:721 (2002))

The area of hyperalgesia (including the uninjured zone) caused by incisions has also been mapped. Secondary hyperalgesia (hyperalgesia outside the injured area) is one measure of enhanced responsiveness of the central nervous system, i.e. central sensitization. It has been noted that the area of flare or redness (possibly a result of axon reflexes) caused by incision was distinct from the area of hyperalgesia. As opposed to pain at rest and primary mechanical hyperalgesia, the large area of hyperalgesia never developed when local anesthetic injection was made before the incision. Moreover, it could not be reversed by local anesthetic injection after incision. In patients after surgery, in some cases, certain treatments greatly reduce the area of hyperalgesia but do not greatly modify clinical measures of post-surgical pain (pain scores and opioid consumption). It has been shown that reducing the area of hyperalgesia after colectomy did not greatly reduce acute pain but was associated with a decrease in the number of patients that developed residual pain even as late as 6 months after colectomy. (De Kock, et al., *Pain* 92:373-80 (2001)).

The use of anti-NGF antibody to treat chronic visceral pain has been described. See PCT Publication No. WO 01/78698. Brennan et al. report administration of TrkA immunoadhesin in a rat model of post-surgical pain. See Society for Neuroscience Abstracts 24(1-2) 880 (1998).

All references cited herein, including patent applications and publications, are incorporated by reference in their entirety.

BRIEF SUMMARY OF THE INVENTION

The present invention is based upon the discovery that an anti-NGF antagonist antibody is effective in treating post-surgical pain. The treatment addresses one or more aspects of post-surgical pain as described herein.

In a first aspect, the invention features a method for preventing or treating post-surgical pain (referred to interchangeably as "post-incisional" or "post-traumatic pain") by administering an anti-NGF antagonist antibody. It has been shown in accordance with the invention that an anti-NGF antagonist antibody (interchangeably referred to as "anti-NGF antibody") is capable of inhibiting or blocking the pain resulting from post-surgical pain, including pain from surgery or from an incisional or traumatic wound.

In another aspect, the invention provides methods for reducing incidence of post-surgical pain, ameliorating post-surgical pain, palliating post-surgical pain; and/or delaying the development or progression of post-surgical pain in an individual, said methods comprising administering an effective amount of an anti-NGF antagonist antibody.

In another aspect, the invention provides methods for increasing pain threshold in an individual comprising administering an effective amount of anti-NGF antagonist antibody.

In another aspect, the invention provides methods for enhancing recovery from surgery and/or injury-induced traumatic wound in an individual comprising administering an effective amount of an anti-NGF antagonist antibody.

In some embodiments, resting pain is suppressed, ameliorated and/or prevented, in some embodiments, mechanically-induced pain (including pain resulting from movement) is suppressed, ameliorated and/or prevented, and in some embodiment, thermally-induced pain is suppressed, ameliorated and/or prevented. In some embodiments, allodynia (i.e., increased response (i.e., increased noxious sensation) to a normally non-noxious stimulus)) is suppressed, ameliorated and/or prevented, and/or hyperalgesia (i.e., increased response to a normally noxious or unpleasant stimulus) is suppressed, ameliorated and/or prevented. In still further embodiments, allodynia and/or hyperalgesia is thermal or mechanical (tactile) in nature, or resting pain. In some embodiments, the pain is chronic pain. In other embodiments, the pain is associated with site of incision, wound or trauma, and/or proximal, at or near the site of incision, wound, and/or trauma.

In some embodiments, the anti-NGF antagonist antibody recognizes human NGF. In yet other embodiments, the anti-NGF antagonist antibody specifically binds human NGF. In some embodiment, the anti-NGF antagonist antibody does not significantly bind to related neurotrophins, such as NT-3, NT4/5, and/or BDNF. In still further embodiments, the anti-NGF antagonist antibody binds essentially the same NGF epitope 6 as an antibody selected from any one or more of the following: MAb 911, MAb 912 and MAb 938 (See Hongo, et al., *Hybridoma* 19:215-227 (2000)). In still other embodiment, the anti-NGF antagonist antibody is a monoclonal antibody. In still other embodiments, the anti-NGF antibody is humanized (such as antibody E3 described herein). In some embodiments, the anti-NGF antibody is antibody E3 (as described herein). In other embodiments, the anti-NGF antibody comprises one or more CDR(s) of antibody E3 (such as one, two, three, four, five, or, in some embodiments, all six CDRs from E3). In other embodiments, the antibody is human. In still other embodiments, the anti-NGF antibody comprises the amino acid sequence of the heavy chain variable region shown in Table 1 (SEQ ID NO:1) and the amino acid sequence of the light chain variable region shown in Table 2 (SEQ ID NO:2). In still other embodiments, the antibody comprises a modified constant region, such as a constant region that is immunologically inert, e.g., does not trigger complement mediated lysis, or does not stimulate antibody-dependent cell mediated cytotoxicity (ADCC). In other embodiments, the constant region is modified as described in Eur. J. Immunol. (1999) 29:2613-2624; PCT Application No. PCT/GB99/01441; and/or UK Patent Application No. 9809951.8.

In other embodiments, the anti-NGF antagonist antibody is an anti-human NGF (anti-hNGF) monoclonal antibody that binds hNGF and effectively inhibits the binding of NGF to its TrkA and/or p75 receptor in vivo and/or effectively inhibiting NGF from activating its TrkA and/or p75 receptor.

The binding affinity of an anti-NGF antagonist antibody to NGF (such as hNGF) can be about 0.10 to about 0.80 nM, about 0.15 to about 0.75 nM and about 0.18 to about 0.72 nM. In one embodiment, the binding affinity is between about 2 pM and 22 pM. In some embodiment, the binding affinity is about 10 nM. In other embodiments, the binding affinity is less than about 10 nM. In other embodiments, the binding affinity is about 0.1 nM or about 0.07 nM. In other embodiments, the binding affinity is less than about 0.1 nM or less than about 0.07 nM. In other embodiments, the binding affinity is any of about 100 nM, about 50 nM, about 10 nM, about 1 nM, about 500 pM, about 100 pM, or about 50 pM to any of about 2 pM, about 5 pM, about 10 pM, about 15 pM, about 20 pM, or about 40 pM. In some embodiments, the binding affinity is any of about 100 nM, about 50 nM, about 10 nM, about 1 nM, about 500 pM, about 100 pM, or about 50 pM, or less than about 50 pM. In some embodiments, the binding affinity is less than any of about 100 nM, about 50 nM, about 10 nM, about 1 nM, about 500 pM, about 100 pM, or about 50 pM. In still other embodiments, the binding affinity is about 2 pM, about 5 pM, about 10 pM, about 15 pM, about 20 pM, about 40 pM, or greater than about 40 pM. As is well known in the art, binding affinity can be expressed as $K_D$, or dissociation constant, and an increased binding affinity corresponds to a decreased $K_D$. The binding affinity of anti-NGF mouse monoclonal antibody 911 (Hongo et al., *Hybridoma* 19:215-227 (2000)) to human NGF is about 10 nM, and the binding affinity of humanized anti-NGF antibody E3 (described herein) to human NGF is about 0.07 nM.

The anti-NGF antagonist antibody may be administered prior to, during and/or after the surgery, incision and/or wound that causes or is associated with the post-surgical pain. In some embodiments, the anti-NGF antagonist antibody is administered prior to the surgery, incision or wound. Administration of an NGF antagonist can be by any means known in the art, including: orally, intravenously, subcutaneously, intraarterially, intramuscularly, intracardially, intraspinally, intrathoracically, intraperitoneally, intraventricularly, sublingually, and/or transdermally. In some embodiments, the NGF antagonist is an anti-NGF antibody, and administration is by one or more of the following means: intravenously, subcutaneously, via inhalation, intraarterially, intramuscularly, intracardially, intraventricularly, and intraperitoneally. Administration may be systemic, e.g. intravenously, or localized.

In a second aspect, the invention features a composition for preventing or treating post-surgical pain comprising an effective amount of an anti-NGF antagonist antibody, in combination with one or more pharmaceutically acceptable excipients.

In a third aspect, the invention features a kit for use in any of the methods described herein. In some embodiments, the kit comprises a container, a composition comprising an anti-NGF antagonist antibody described herein, in combination with a pharmaceutically acceptable carrier, and instructions for using the composition in any of the methods described herein.

BRIEF DESCRIPTION OF THE DRAWING(S)

FIG. 1 is a graph depicting cumulative resting pain as assessed 24 hours before surgery ("baseline"), 2 hours after surgery ("post-surgery") and 1, and 2 days after surgery. "Control" refers to no anti-NGF antibody treatment, and "911" refers to animals treated with 35 mg/kg anti-NGF antibody 911 (also called "Mab 911"). Hongo et al., *Hybridoma* 19:215-227 (2000). Treatment with anti-NGF antibody significantly reduced post-surgical resting pain.

FIG. 2 is a graph depicting thermal pain (hyperalgesia) as assessed 24 hours before surgery ("baseline"), 4 hours after surgery ("post-surgery") and 1 and 2 days after surgery. "Control" refers to no anti-NGF antibody treatment, and "911" refers to animals treated with 35 mg/kg anti-NGF antibody 911. Treatment with anti-NGF antibody significantly reduced post-surgical thermal hyperalgesia.

FIG. 3 is a graph depicting mechanical pain (hyperalgesia) in response to mechanical stimulation as assessed 24 hours before surgery ("baseline"), 3 hours after surgery ("post-surgery") and 1, 2 and 3 days after surgery. "Control" refers to no anti-NGF treatment, and "911" refers to animals treated with anti-NGF antibody 911. Treatment with 7 mg/kg anti-NGF antibody reduced post-surgical mechanically-induced pain.

Figure 6:
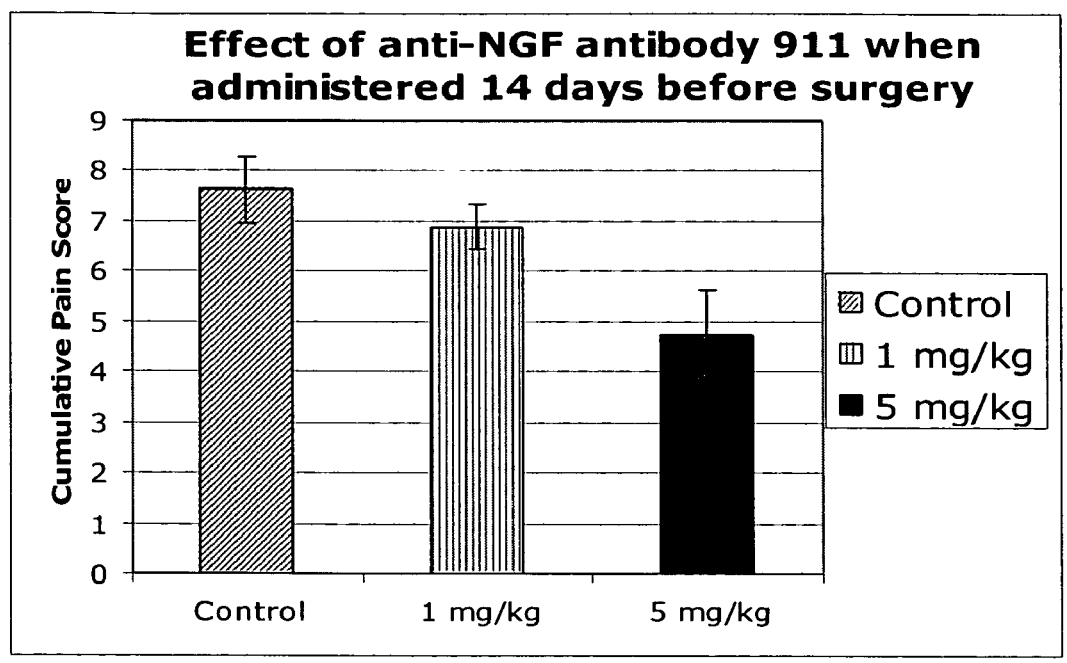

FIG. 6 is a graph depicting resting pain assessed 24 hours after surgery and showing that treatment with 5 mg/kg anti-NGF antibody 911 significantly reduced resting pain ($p<0.02$) when injected 14 days pre-surgery.

Figure 7:
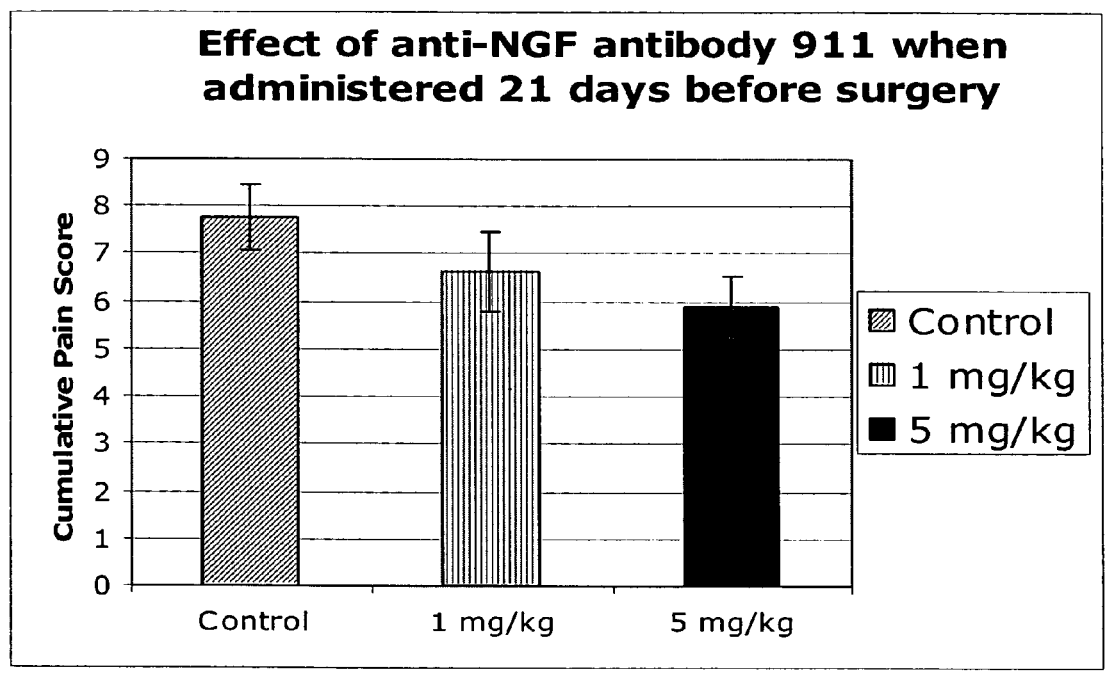

FIG. 7 is a graph depicting resting pain assessed 24 hours after surgery and showing that treatment with 5 mg/kg anti-NGF antibody 911 reduced resting pain when injected 21 days pre-surgery.

Figure 8:
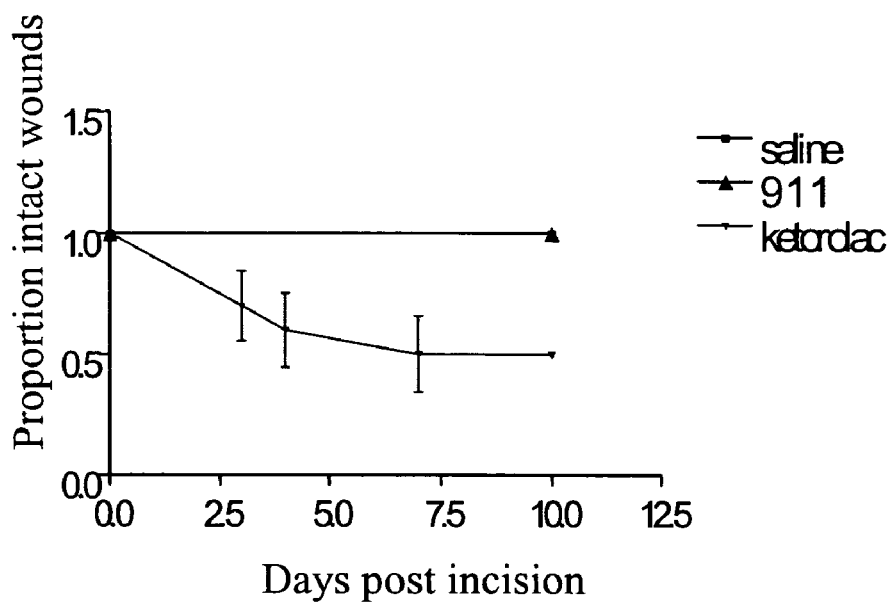

FIG. 8 is a graph depicting proportion of intact wounds present after incision and treatment with saline, 1 mg/kg anti-NGF antibody 911, or the positive control, ketorolac. The proportion of intact wounds following treatment with anti-NGF antibody 911 did not differ from the proportion of intact wounds following treatment with saline (negative control). Thus, treatment with anti-NGF antibody showed no effect on wound healing. By contrast, animals treated with the NSAID ketorolac (positive control) showed significantly reduced proportion of intact wounds.

Figure 9:
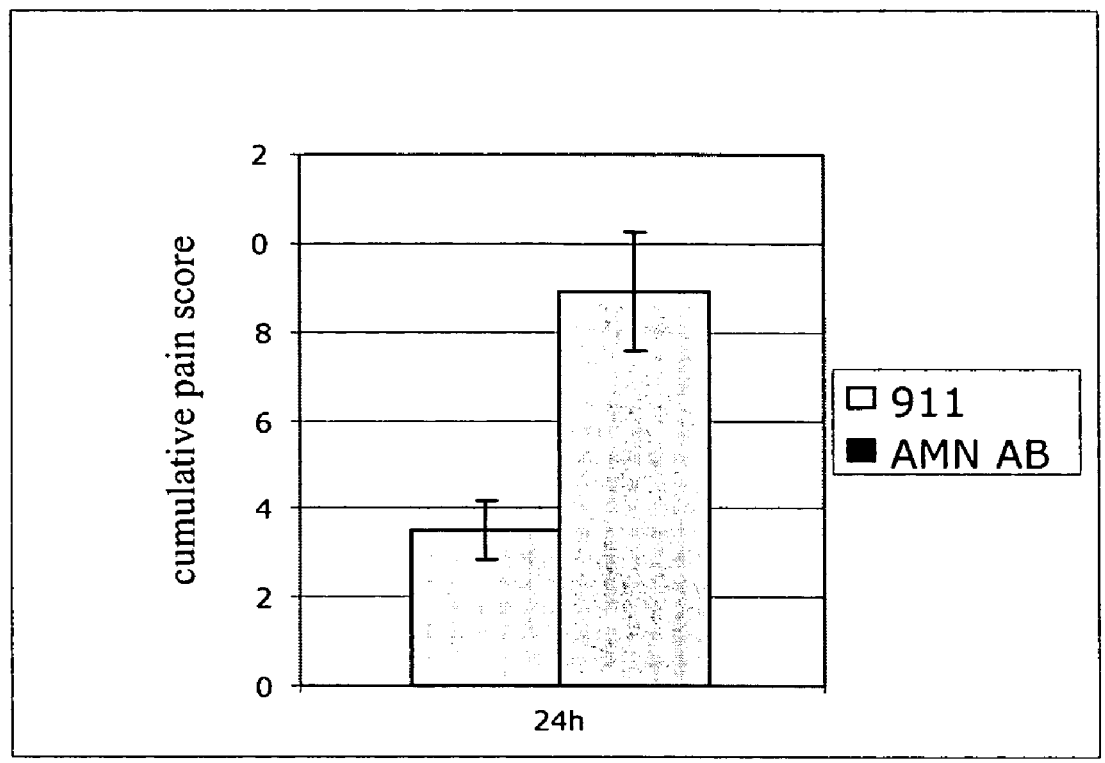

FIG. 9 is a graph comparing treatment with anti-NGF antibody, 911, and treatment with an isotype matched control antibody. Animals treated with 1 mg/kg of anti-NGF antibody (911) showed significantly reduced resting pain ($p<0.05$). By contrast, animals treated with 1 mg/kg of an isotype matched control antibody to the *Drosophila* amnesiac protein displayed normal levels of resting pain. This experiment demonstrated that the analgesic effect of the anti-NGF antibody was specific.

DETAILED DESCRIPTION OF THE INVENTION

The present invention is based on the discovery that in vivo administration of a therapeutically effective amount of an anti-NGF antagonist antibody may be used to prevent and/or treat post-surgical pain. Post-operative pain has been previously treated with high doses of opioid analgesics. These agents cause undesirable side effects such as decreased gastric motility, sedation, respiratory depression and renal colic. Other pain agents, such as NSAIDs, have been relatively unsuccessful in treating this type of pain. Further, some NSAIDs are known to inhibit wound healing.

The invention features a method of preventing or treating post-surgical pain in an individual (including a mammal, both human and non-human) by administering an effective amount of an anti-NGF antagonist antibody, for instance an anti-human NGF (anti-hNGF) monoclonal antibody.

In another aspect, the invention provides methods for ameliorating, delaying the development of and/or preventing the progression of post-surgical pain comprising administering an effective amount of an anti-NGF antagonist antibody to an individual.

In some embodiments, resting pain is suppressed, ameliorated and/or prevented, and in some embodiments, mechanically-induced pain (such as pain resulting from movement or other mechanical or tactile stimulation) is suppressed, ameliorated and/or prevented. In some embodiment, thermally-induced pain is suppressed, ameliorated and/or prevented. In some embodiments, allodynia is suppressed, ameliorated and/or prevented, and in some embodiments, hyperalgesia is suppressed, ameliorated and/or prevented. In still further embodiments, allodynia and/or hyperalgesia is thermal or mechanical (tactile) in nature, or resting pain. In some embodiments, the pain is chronic pain. In other embodiments, the pain is at, proximal, and/or near to one or more site(s) of incision, wound or trauma.

In some embodiments, the anti-NGF antagonist antibody recognizes human NGF. In yet other embodiments, the anti-NGF antagonist antibody specifically binds human NGF. In some embodiment, the anti-NGF antagonist antibody does not significantly bind to related neurotrophins, such as NT-3, NT4/5, and/or BDNF. In still further embodiments, the anti-NGF antagonist antibody binds essentially the same NGF epitope 6 as an antibody selected from any one or more of the following: MAb 911, MAb 912 and MAb 938 (See Hongo, et al., *Hybridoma* 19:215-227 (2000)). In other embodiments, the antibody bids the same epitope as Mab 911. In still other embodiments, the anti-NGF antibody is capable of binding NGF and effectively inhibiting the binding of NGF to its TrkA and/or p75 receptor in vivo and/or effectively inhibiting NGF from activating its TrkA and/or p75 receptor. In still other embodiment, the anti-NGF antagonist antibody is a monoclonal antibody. In still other embodiments, the anti-NGF antibody is humanized (such as antibody E3 described herein). In some embodiments, the anti-NGF antibody is antibody E3 (as described herein). In other embodiments, the anti-NGF antibody comprises one or more CDR(s) of antibody E3 (such as one, two, three, four, five, or, in some embodiments, all six CDRs from E3). In other embodiments, the antibody is human. In still other embodiments, the anti-NGF antibody comprises the amino acid sequence of the heavy chain variable region shown in Table 1 (SEQ ID NO:1) and the amino acid sequence of the light chain variable region shown in Table 2 (SEQ ID NO:2). In still other embodiments, the antibody comprises a modified constant region, such as a constant region that is immunologically inert, e.g., does not trigger complement mediated lysis, or does not stimulate antibody-dependent cell mediated cytotoxicity (ADCC). In other embodiments, the constant region is modified as described in Eur. J. Immunol. (1999) 29:2613-2624; PCT Application No. PCT/GB99/01441; and/or UK Patent Application No. 9809951.8.

In other embodiments, the anti-NGF antagonist antibody is an anti-human NGF (anti-hNGF) monoclonal antibody that binds hNGF and effectively inhibits the binding of NGF to its TrkA and/or p75 receptor in vivo and/or effectively inhibiting NGF from activating its TrkA and/or p75 receptor.

The binding affinity of an anti-NGF antagonist antibody to NGF (such as hNGF) can be about 0.10 nM to about 1.00 nM, about 0.10 nM to about 0.80 nM, about 0.15 to about 0.75 nM and about 0.18 to about 0.72 nM. In one embodiment, the binding affinity is between about 2 pM and 22 pM. In some embodiment, the binding affinity is about 10 nM. In other embodiments, the binding affinity is less than about 10 nM. In other embodiments, the binding affinity is about 0.1 nM. In other embodiments, the binding affinity is less than about 0.1 nM. In other embodiments, the binding affinity is any of about 100 nM, about 50 nM, about 10 nM, about 1 nM, about 500 pM, about 100 pM, or about 50 pM to any of about 2 pM, about 5 pM, about 10 pM, about 15 pM, about 20 pM, or about 40 pM. In some embodiments, the binding affinity is any of about 100 nM, about 50 nM, about 10 nM, about 1 nM, about 500 pM, about 100 pM, or about 50 pM, or less than about 50 pM. In some embodiments, the binding affinity is less than any of about 100 nM, about 50 nM, about 10 nM, about 1 nM, about 500 pM, about 100 pM, or about 50 pM. In still other embodiments, the binding affinity is about 2 pM, about 5 pM, about 10 pM, about 15 pM, about 20 pM, about 40 pM, or greater than about 40 pM. As is well known in the art, binding affinity can be expressed as $K_D$, or dissociation constant, and an increased binding affinity corresponds to a decreased $K_D$. The binding affinity of anti-NGF mouse monoclonal antibody 911 (Hongo et al., *Hybridoma* 19:215-227 (2000)) to human NGF is about 10 nM, and the binding affinity of humanized anti-NGF antibody E3 (described herein) to human NGF is about 0.1 nM.

The antibody may also be an antibody fragment, including an antibody fragment selected from one or more of the following: of Fab, Fab', F(ab')2, Fv fragments, diabodies, single chain antibody molecules and multispecific antibodies formed from antibody fragments, and a single-chain Fv (scFv) molecule. The antibody may also be chimeric, and it may be humanized or human. The antibody may also be bispecific.

Administration of an anti-NGF antagonist antibody can be by any means known in the art, including: intravenously, subcutaneously, via inhalation, intraarterially, intramuscularly, intracardially, intraventricularly, parenteral, and intraperitoneally. Administration may be systemic, e.g. intravenously, or localized.

The invention also features compositions and kits for treating post-surgical pain comprising an anti-NGF antagonist antibody, for instance an anti-NGF monoclonal antibody, for use in ant of the methods described herein. In some embodiments, the anti-NGF antagonist antibody is capable of effectively inhibiting NGF binding TrkA or p75 and/or of effectively inhibiting NGF from activating its TrkA and/or p75 receptor.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook, et al., 1989) Cold Spring Harbor Press; *Oligonucleotide Synthesis* (M. J. Gait, ed., 1984); *Methods in Molecular Biology, Humana Press; Cell Biology: A Laboratory Notebook* (J. E. Cellis, ed., 1998) Academic Press; *Animal Cell Culture* (R. I. Freshney, ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Methods in Enzymology* (Academic Press, Inc.); *Handbook of Experimental Immunology* (D. M. Weir and C. C. Blackwell, eds.); *Gene Transfer Vectors for Mammalian Cells* (J. M. Miller and M. P. Calos, eds., 1987); *Current Protocols in Molecular Biology* (F. M. Ausubel, et al., eds., 1987); *PCR: The Polymerase Chain Reaction*, (Mullis, et al., eds., 1994);

*Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: a practical approach* (D. Catty., ed., IRL Press, 1988-1989); *Monoclonal antibodies: a practical approach* (P. Shepherd and C. Dean, eds., Oxford University Press, 2000); *Using antibodies: a laboratory manual* (E. Harlow and D. Lane (Cold Spring Harbor Laboratory Press, 1999); *The Antibodies* (M. Zanetti and J. D. Capra, eds., Harwood Academic Publishers, 1995).

Definitions

An "antibody" (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')2, Fv), single chain (ScFv), mutants thereof, fusion proteins comprising an antibody portion, humanized antibodies, chimeric antibodies, diabodies linear antibodies, single chain antibodies, multispecific antibodies (e.g., bispecific antibodies) and any other modified configuration of the immunoglobulin molecule that comprises an antigen recognition site of the required specificity. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

A "monoclonal antibody" refers to a homogeneous antibody population wherein the monoclonal antibody is comprised of amino acids (naturally occurring and non-naturally occurring) that are involved in the selective binding of an antigen. A population of monoclonal antibodies is highly specific, being directed against a single antigenic site. The term "monoclonal antibody" encompasses not only intact monoclonal antibodies and full-length monoclonal antibodies, but also fragments thereof (such as Fab, Fab', F(ab')2, Fv), single chain (ScFv), mutants thereof, fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.).

"Humanized" antibodies refer to a molecule having an antigen binding site that is substantially derived from an immunoglobulin from a non-human species and the remaining immunoglobulin structure of the molecule based upon the structure and/or sequence of a human immunoglobulin. The antigen binding site may comprise either complete variable domains fused onto constant domains or only the complementarity determining regions (CDRs) grafted onto appropriate framework regions in the variable domains. Antigen binding sites may be wild type or modified by one or more amino acid substitutions, e.g., modified to resemble human immunoglobulin more closely. Some forms of humanized antibodies preserve all CDR sequences (for example, a humanized mouse antibody which contains all six CDRs from the mouse antibodies). Other forms of humanized antibodies have one or more CDRs (one, two, three, four, five, six) which are altered with respect to the original antibody. In some instances, framework region (FR) residues or other residues of the human immunoglobulin replaced by corresponding non-human residues. Furthermore, humanized antibodies may comprise residues which are not found in the recipient antibody or in the donor antibody.

As used herein, the term "nerve growth factor" and "NGF" refers to nerve growth factor and variants thereof that retain at least part of the activity of NGF. As used herein, NGF includes all mammalian species of native sequence NGF, including human, canine, feline, equine, or bovine.

"NGF receptor" refers to a polypeptide that is bound by or activated by NGF. NGF receptors include the TrkA receptor and the p75 receptor of any mammalian species, including, but are not limited to, human, canine, feline, equine, primate, or bovine.

As used herein, an "anti-NGF antagonist antibody" (interchangeably termed "anti-NGF antibody") refers to an antibody which is able to bind to NGF and inhibit NGF biological activity and/or downstream pathway(s) mediated by NGF signaling. An anti-NGF antagonist antibody encompasses antibodies that block, antagonize, suppress or reduce (including significantly) NGF biological activity, including downstream pathways mediated by NGF signaling, such as receptor binding and/or elicitation of a cellular response to NGF. For purpose of the present invention, it will be explicitly understood that the term "anti-NGF antagonist antibody" encompass all the previously identified terms, titles, and functional states and characteristics whereby the NGF itself, an NGF biological activity (including but not limited to its ability to ability to mediate any aspect of post-surgical pain), or the consequences of the biological activity, are substantially nullified, decreased, or neutralized in any meaningful degree. In some embodiment, an anti-NGF antagonist antibody binds NGF and prevent NGF dimerization and/or binding to an NGF receptor (such as p75 and/or trkA). In other embodiments, an anti-NGF antibody binds NGF and prevents trkA receptor dimerization and/or trkA autophosphorylation. Examples of anti-NGF antagonist antibodies are provided herein.

A "TrkA immunoadhesin" refers to a soluble chimeric molecule comprising a fragment of a TrkA receptor, for example, the extracellular domain of a TrkA receptor and an immunoglobulin sequence, which retains the binding specificity of the TrkA receptor.

"Biological activity" of NGF generally refers to the ability to bind NGF receptors and/or activate NGF receptor signaling pathways. Without limitation, a biological activity includes any one or more of the following: the ability to bind an NGF receptor (such as p75 and/or TrkA); the ability to promote TrkA receptor dimerization and/or autophosphorylation; the ability to activate an NGF receptor signaling pathway; the ability to promote cell differentiation, proliferation, survival, growth and other changes in cell physiology, including (in the case of neurons, including peripheral and central neuron) change in neuronal morphology, synaptogenesis, synaptic function, neurotransmitter and/or neuropeptide release and regeneration following damage; and the ability to mediate post-surgical pain.

The term "epitope" is used to refer to binding sites for (monoclonal or polyclonal) antibodies on protein antigens.

As used herein, "treatment" is an approach for obtaining beneficial or desired clinical results. For purposes of this invention, beneficial or desired clinical results include, but are not limited to, one or more of the following: improvement in any aspect of the pain including lessening severity, alleviation of one or more symptoms associated with post-surgical pain including any aspect of post-surgical pain (such as resting pain and/or mechanically-induced pain, shortening duration of pain, and/or reduction of pain sensitivity or sensation). An "effective amount" is an amount sufficient to effect beneficial or desired clinical results including alleviation or reduction in pain. For purposes of this invention, an effective amount of an anti-NGF antagonist antibody is an amount sufficient to treat, ameliorate, reduce the intensity of or prevent post-surgical pain. In some embodiments, the "effective amount" may reduce pain at rest (resting pain) or mechanically-induced pain (including pain following movement, or both, and it may be administered before, during and/or after an incision, cut, tear or injury. In some embodiment, the "effective amount" is an amount sufficient to delay development of post-surgical pain.

"Reducing incidence" of pain means any of reducing severity (which can include reducing need for and/or amount of (e.g., exposure to) other drugs and/or therapies generally used for this conditions, including, for example, opiates), duration, and/or frequency (including, for example, delaying or increasing time to post-surgical pain in an individual). As is understood by those skilled in the art, individuals may vary in terms of their response to treatment, and, as such, for example, a "method of reducing incidence of post-surgical pain in an individual" reflects administering the anti-NGF antagonist antibody based on a reasonable expectation that such administration may likely cause such a reduction in incidence in that particular individual.

"Ameliorating" post-surgical pain or one or more symptoms of post-surgical pain means a lessening or improvement of one or more symptoms of a post-surgical pain as compared to not administering an anti-NGF antagonist antibody. "Ameliorating" also includes shortening or reduction in duration of a symptom.

"Palliating" post-surgical pain or one or more symptoms of a post-surgical pain means lessening the extent of one or more undesirable clinical manifestations of post-surgical pain in an individual or population of individuals treated with an anti-NGF antagonist antibody in accordance with the invention.

As used therein, "delaying" the development of post-surgical pain means to defer, hinder, slow, retard, stabilize, and/or postpone progression of post-surgical pain. This delay can be of varying lengths of time, depending on the history of the disease and/or individuals being treated. As is evident to one skilled in the art, a sufficient or significant delay can, in effect, encompass prevention, in that the individual does not develop post-surgical pain. A method that "delays" development of the symptom is a method that reduces probability of developing the symptom in a given time frame and/or reduces extent of the symptoms in a given time frame, when compared to not using the method. Such comparisons are typically based on clinical studies, using a statistically significant number of subjects.

"Development" or "progression" of post-surgical pain means initial manifestations and/or ensuing progression of the disorder. Development of post-surgical pain can be detectable and assessed using standard clinical techniques as well known in the art. However, development also refers to progression that may be undetectable. For purpose of this invention, development or progression refers to the biological course of the symptoms. "Development" includes occurrence, recurrence, and onset. As used herein "onset" or "occurrence" of post-surgical pain includes initial onset and/or recurrence.

An "individual" is a vertebrate, preferably a mammal, more preferably a human. Mammals include, but are not limited to, farm animals, sport animals, pets, primates, horses, dogs, cats, mice and rats.

"Post-surgical pain" (interchangeably termed "post-incisional" or "post-traumatic pain") refers to pain arising or resulting from an external trauma such as a cut, puncture, incision, tear, or wound into tissue of an individual (including that that arises from all surgical procedures, whether invasive or non-invasive). As used herein, "post-surgical pain" does not include pain that occurs without an external physical trauma. In some embodiments, post-surgical pain is internal or external pain, and the wound, cut, trauma, tear or incision may occur accidentally (as with a traumatic wound) or deliberately (as with a surgical incision). As used herein, "pain" includes nociception and the sensation of pain, and pain can be assessed objectively and subjectively, using pain scores and other methods well-known in the art. Post-surgical pain, as used herein, includes allodynia (i.e., increased response to a normally non-noxious stimulus) and hyperalgesia (i.e., increased response to a normally noxious or unpleasant stimulus), which can in turn, be thermal or mechanical (tactile) in nature. In some embodiments, the pain is characterized by thermal sensitivity, mechanical sensitivity and/or resting pain. In some embodiments, the post-surgical pain comprises mechanically-induced pain or resting pain. In other embodiments, the post-surgical pain comprises resting pain. The pain can be primary or secondary pain, as is well-known in the art.

"Resting pain" refers to pain occurring even while the individual is at rest as opposed to, for example, pain occurring when the individual moves or is subjected to other mechanical stimuli (for example, poking or prodding).

"Mechanically-induced pain" (interchangeably termed mechanosensory pain) refers to pain induced by a mechanical stimulus, such as the application of weight to a surface, tactile stimulus, and stimulation caused or associated with movement (including coughing, shifting of weight, etc.).

Recovery from surgery, trauma or wound is "enhanced" when an aspect of recovery from surgery, trauma, or wound is improved (as compared to recovery from surgery, trauma or wound without administering an NGF antagonist). For example, the presence and/or intensity of undesired side-effects (such as side-effects associated with use of conventional pain relievers (e.g. opioid) may be reduced and/or eliminated in the presence of an NGF antagonist relative to the presence and/or intensity of such side-effects in the absence of an NGF antagonist. This enhancement is indicated by administration of an NGF antagonist and is not meant to convey that such a comparison (administration of an NGF antagonist verses no administration) must be conducted and proven with respect to any given individual.

Methods of the Invention

With respect to all methods described herein, reference to anti-NGF antagonist antibodies also include compositions comprising one or more of these agents. These compositions may further comprise suitable excipients, such as pharmaceutically acceptable excipients including buffers, which are well known in the art. The present invention can be used alone or in combination with other conventional methods of treatment.

Methods for Preventing or Treating Post-Surgical Pain

The present invention is useful for treating, delaying development of and/or preventing post-surgical pain in individuals including all mammals, both human and non-human. Moreover, the present invention is useful in individuals having an incisional wound to tissue whether a cut, puncture or tear, whether internal or external. Such an incisional wound may occur accidentally as with traumatic wound or deliberately as with surgery.

Accordingly, in one aspect, the invention provides methods of treating post-surgical pain in an individual comprising administering an effective amount of an anti-NGF antagonist antibody. In some embodiments, the post-surgical pain comprises one or more of: allodynia, hyperalgesia, mechanically-induced pain, thermally-induced pain, thermally induced pain, mechanically induced pain, or resting pain. In some embodiments, the post-surgical pain comprises mechanically-induced pain and/or resting pain. We have observed, for example, that anti-NGF antagonist antibodies alleviate both of these aspects. In other embodiments, the post-surgical pain comprises resting pain. The pain can be primary and/or secondary pain. In other embodiments, allodynia is suppressed, ameliorated and/or prevented, and in some embodiments, hyperalgesia is suppressed, ameliorated and/or prevented. In still further embodiments, allodynia and/or hyperalgesia is thermal or mechanical (tactile) in nature (or both), or resting pain. In some embodiments, the pain is chronic pain. In other embodiments, the pain is at, proximal and/or near to one or more site(s) of incision, wound or trauma.

In another aspect, the invention provides methods of preventing, ameliorating and/or preventing the development or progression of post-surgical pain. administered prior to surgery (in some embodiment, prior to activity likely to result in external trauma and/or wound). For example, the anti-NGF antagonist antibody can be administered 30 minutes, one hour, 5 hours, 10 hours, 15 hours, 24 hours or even more, such as 1 day, several days, or even a week, two weeks, three weeks, or more prior to the activity with a risk of trauma, wound or incision, or prior to an operation (in some embodiment, likely to result in trauma, wound or incision). In other embodiments, the anti-NGF antagonist antibody is administered during and/or after surgery or activity likely to result in external trauma or wound. In one embodiment, the anti-NGF antagonist antibody is administered 1 hour, 2 hours, 3 hours, 4 hours, 6 hours, 8 hours, 12 hours, 24 hours, 30 hours, 36 hours, or more, after surgery, wound, or trauma.

In another aspect, the invention provides methods for increasing pain threshold. As used herein, "increasing pain threshold" refers to a reduction, diminishment and/or minimization of pain associated with surgery, incision, trauma or wound (including reduced, diminished, and/or minimized subjective perception of pain).

In yet another aspect, the invention provides methods for enhancing recovery from surgery (as well as enhancing recovery from wound, traumatic injury, and/or incision).

It is appreciated that although reference is generally made herein to treating or preventing post-surgical pain, the anti-NGF antagonist antibody can be administered before an event or condition(s) with an increased risk of external trauma (such as an impact), injury, or wound. As is understood by one skilled in the art, an event or condition with increased risk of external trauma, injury or wound encompasses dangerous vocations, combat, and/or sporting activities.

Diagnosis or assessment of pain is well-established in the art. Assessment may be performed based on objective measure, such as observation of behavior such as reaction to stimuli, facial expressions and the like. Assessment may also be based on subjective measures, such as patient characterization of pain using various pain scales. See, e.g., Katz et al, Surg Clin North Am. (1999) 79 (2):231-52; Caraceni et al. J Pain Symptom Manage (2002) 23(3):239-55.

Pain relief may also be characterized by time course of relief. Accordingly, in some embodiments, pain relief is subjectively or objectively observed after 1, 2, or a few hours (and in some embodiments, peaks at about 12-18 hours). In another embodiment, pain relief is subjectively or objectively observed at 24, 36, 48, 60 72 or more hours following surgery (or event associated with wound or trauma).

Anti-NGF Antagonist Antibody

The methods of the invention use an anti-NGF antagonist antibody, which refers to any antibody molecule that blocks, suppresses or reduces (including significantly) NGF biological activity, including downstream pathways mediated by NGF signaling, such as receptor binding and/or elicitation of a cellular response to NGF.

An anti-NGF antagonist antibody should exhibit any one or more of the following characteristics: (a) bind to NGF; (b) inhibit NGF biological activity or downstream pathways mediated by NGF signaling function; (c) prevent, ameliorate, or treat any aspect of post-surgical pain; (d) block or decrease NGF receptor activation (including TrkA receptor dimerization and/or autophosphorylation); (e) increase clearance of NGF; (f) inhibit (reduce) NGF synthesis, production or release; (g) enhance recovery from surgery, wound or trauma. Anti-NGF antagonist antibodies are known in the art, see, e.g., PCT Publication Nos. WO 01/78698, WO 01/64247, U.S. Pat. Nos. 5,844,092, 5,877, 016, and 6,153,189; Hongo et al., *Hybridoma*, 19:215-227 (2000); *Cell. Molec. Biol.* 13:559-568 (1993); GenBank Accession Nos. U39608, U39609, L17078, or L17077.

For purposes of this invention, the antibody reacts with NGF in a manner that inhibits NGF and/or downstream pathways mediated by the NGF signaling function. In some embodiments, the anti-NGF antagonist antibody recognizes human NGF. In yet other embodiments, the anti-NGF antagonist antibody specifically binds human NGF. In some embodiment, the anti-NGF antagonist antibody does not significantly bind to related neurotrophins, such as NT-3, NT4/5, and/or BDNF. In still other embodiments, the anti-NGF antibody is capable of binding NGF and effectively inhibiting the binding of NGF to its TrkA and/or p75 receptor in vivo and/or effectively inhibiting NGF from activating its TrkA and/or p75 receptor. In still other embodiment, the anti-NGF antagonist antibody is a monoclonal antibody. In still other embodiments, the anti-NGF antibody is humanized (such as antibody E3 described herein). In some embodiments, the anti-NGF antibody is human. In one embodiment, the antibody is a human antibody which recognizes one or more epitopes on human NGF. In another embodiment, the antibody is a mouse or rat antibody which recognizes one or more epitopes on human NGF. In another embodiment, the antibody recognizes one or more epitopes on an NGF selected from the group consisting of: primate, canine, feline, equine, and bovine. In still further embodiments, the anti-NGF antagonist antibody binds essentially the same NGF epitope 6 as an antibody selected from any one or more of the following: MAb 911, MAb 912 and MAb 938 (See Hongo, et al., *Hybridoma* 19:215-227 (2000)). In other embodiments, the antibody bids the same epitope as Mab 911. In another embodiment, the antibody comprises a constant region that is immunologically inert (e.g., does not trigger complement mediated lysis or antibody dependent cell mediated cytotoxicity (ADCC)). ADCC activity can be assessed using methods disclosed in U.S. Pat. No. 5,500, 362. In some embodiments, the constant region is modified as described in Eur. J. Immunol. (1999) 29:2613-2624; PCT Application No. PCT/GB99/01441; and/or UK Patent Application No. 9809951.8.

In some embodiments, the anti-NGF antibody is a humanized mouse anti-NGF monoclonal antibody termed antibody "E3", which comprises the human heavy chain IgG2a constant region containing the following mutations: A330P331 to S330S331 (amino acid numbering with reference to the wildtype IgG2a sequence; see Eur. J. Immunol. (1999) 29:2613-2624); the human light chain kappa constant region; heavy and light chain variable regions shown in Tables 1 and 2.

TABLE 1

Heavy chain variable region

QVQLQESGPGLVKPSETLSLTCTVSGFSLIGYDLNWIRQPPGKGLE
WIGIIWGDGTTDYNSAVKSRVTISKDTSKNQFSLKLSSVTAADTAV
YYCARGGYWYATSYYFDYWGQGTLVTVS (SEQ ID NO:1).

TABLE 2

Light chain variable region

DIQMTQSPSSLSASVGDRVTITCRASQSISNNLNWYQQKPGKAPKLL
IYYTSRFHSGVPSRFSGSGSGTDFTFTISSLQPEDIATYYCQQEHTLP
YTFGQGTKLEIKRT (SEQ ID NO:2).

The following polynucleotides encoding the heavy chain variable region or the light chain variable region were deposited at the ATCC on Jan. 8, 2003:

| Material | | ATCC Accession No. | Date of Deposit |
|---|---|---|---|
| Vector Eb.911.3E | E3 light chain V region | PTA-4893 | Jan. 8, 2003 |
| Vector Eb.pur.911.3E | E3 light chain V region | PTA-4894 | Jan. 8, 2003 |
| Vector Db.911.3E | E3 heavy chain V region | PTA-4895 | Jan. 8, 2003 |

Vector Eb.911.3E is a polynucleotide encoding the light chain variable region shown in Table 2; vector Eb.pur.911.3E is a polynucleotide encoding the light chain variable region shown in Table 2 and vector Db.911.3E is a polynucleotide encoding the heavy chain variable region shown in Table 1.

In another embodiment, the anti-NGF antibody comprises one or more CDR(s) of antibody E3 (such as one, two, three, four, five, or, in some embodiments, all six CDRs from E3). Determination of CDR regions is well within the skill of the art.

The antibodies useful in the present invention can encompass monoclonal antibodies, polyclonal antibodies, antibody fragments (e.g., Fab, Fab', F(ab')2, Fv, Fc, etc.), chimeric antibodies, bispecific antibodies, heteroconjugate antibodies, single chain (ScFv), mutants thereof, fusion proteins comprising an antibody portion, humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies).

The binding affinity of an anti-NGF antagonist antibody to NGF (such as hNGF) can be about 0.10 to about 0.80 nM, about 0.15 to about 0.75 nM and about 0.18 to about 0.72 nM. In one embodiment, the binding affinity is between about 2 pM and 22 pM. In some embodiment, the binding affinity is about 10 nM. In other embodiments, the binding affinity is less than about 10 nM. In other embodiments, the binding affinity is about 0.1 nM or about 0.07 nM. In other embodiments, the binding affinity is less than about 0.1 nM or less than about 0.07 nM. In other embodiments, the binding affinity is any of about 100 nM, about 50 nM, about 10 nM, about 1 nM, about 500 pM, about 100 pM, or about 50 pM to any of about 2 pM, about 5 pM, about 10 pM, about 15 pM, about 20 pM, or about 40 pM. In some embodiments, the binding affinity is any of about 100 nM, about 50 nM, about 10 nM, about 1 nM, about 500 pM, about 100 pM, or about 50 pM, or less than about 50 pM. In some embodiments, the binding affinity is less than any of about 100 nM, about 50 nM, about 10 nM, about 1 nM, about 500 pM, about 100 pM, or about 50 pM. In still other embodiments, the binding affinity is about 2 pM, about 5 pM, about 10 pM, about 15 pM, about 20 pM, about 40 pM, or greater than about 40 pM.

One way of determining binding affinity of antibodies to NGF is by measuring binding affinity of monofunctional Fab fragments of the antibody. To obtain monofunctional Fab fragments, an antibody (for example, IgG) can be cleaved with papain or expressed recombinantly. The affinity of an anti-NGF Fab fragment of an antibody can be determined by surface plasmon resonance (BIAcore3000™ surface plasmon resonance (SPR) system, BIAcore, INC, Piscaway N.J.). CM5 chips can be activated with N-ethyl-N'-(3-dimethylaminopropyl)-carbodiimide hydrochloride (EDC) and N-hydroxysuccinimide (NHS) according to the supplier's instructions. Human NGF (or any other NGF) can be diluted into 10 mM sodium acetate pH 4.0 and injected over the activated chip at a concentration of 0.005 mg/mL. Using variable flow time across the individual chip channels, two ranges of antigen density can be achieved: 100-200 response units (RU) for detailed kinetic studies and 500-600 RU for screening assays. The chip can be blocked with ethanolamine. Regeneration studies have shown that a mixture of Pierce elution buffer (Product No. 21004, Pierce Biotechnology, Rockford Ill.) and 4 M NaCl (2:1) effectively removes the bound Fab while keeping the activity of hNGF on the chip for over 200 injections. HBS-EP buffer (0.01M HEPES, pH 7.4, 0.15 NaCl, 3 mM EDTA, 0.005% Surfactant P29) is used as running buffer for the BIAcore assays. Serial dilutions (0.1-10× estimated $K_D$) of purified Fab samples are injected for 1 min at 100 µL/min and dissociation times of up to 2 h are allowed. The concentrations of the Fab proteins are determined by ELISA and/or SDS-PAGE electrophoresis using a Fab of known concentration (as determined by amino acid analysis) as a standard. Kinetic association rates ($k_{on}$) and dissociation rates ($k_{off}$) are obtained simultaneously by fitting the data to a 1:1 Langmuir binding model (Karlsson, R. Roos, H. Fagerstam, L. Petersson, B. (1994). Methods Enzymology 6. 99-110) using the BIAevaluation program. Equilibrium dissociation constant ($K_D$) values are calculated as $k_{off}/k_{on}$. This protocol is suitable for use in determining binding affinity of an antibody to any NGF, including human NGF, NGF of another vertebrate (in some embodiments, mammalian) (such as mouse NGF, rat NGF, primate NGF), as well as for use with other neurotrophins, such as the related neurotrophins NT3, NT4/5, and/or BDNF.

In some embodiments, the antibody binds human NGF, and does not significantly bind an NGF from another vertebrate species (in some embodiment, mammalian). In some embodiments, the antibody binds human NGF as well as one or more NGF from another vertebrate species (in some embodiments, mammalian). In still other embodiments, the antibody binds NGF and does not significantly cross-react with other neurotrophins (such as the related neurotrophins, NT3, NT4/5, and/or BDNF). In some embodiments, the antibody binds NGF as well as at least one other neurotrophin. In some embodiments, the antibody binds to a mammalian species of NGF, such as horse or dog, but does not significantly bind to NGF from anther mammalian species.

The epitope(s) can be continuous or discontinuous. In one embodiment, the antibody binds essentially the same hNGF epitopes as an antibody selected from the group consisting of MAb 911, MAb 912, and MAb 938 as described in Hongo et al., *Hybridoma*, 19:215-227 (2000). In another embodiment, the antibody binds essentially the same hNGF epitope as MAb 911. In still another embodiment, the antibody binds essentially the same epitope as MAb 909. Hongo et al., supra. For example, the epitope may comprise one or more of: residues K32, K34 and E35 within variable region 1 (amino acids 23-35) of hNGF; residues F79 and T81 within variable region 4 (amino acids 81-88) of hNGF; residues H84 and K88 within variable region 4; residue R103 between variable region 5 (amino acids 94-98) of hNGF and the C-terminus (amino acids 111-118) of hNGF; residue E11 within pre-variable region 1 (amino acids 10-23) of hNGF; Y52 between variable region 2 (amino acids 40-49) of hNGF and variable region 3 (amino acids 59-66) of hNGF; residues L112 and S113 within the C-terminus of hNGF; residues R59 and R69 within variable region 3 of hNGF; or residues V18, V20, and G23 within pre-variable region 1 of hNGF. In addition, an epitope can comprise one or more of the variable region 1, variable region 3, variable region 4, variable region 5, the N-terminus region, and/or the C-terminus of hNGF. In still another embodiment, the antibody significantly reduces the solvent accessibility of residue R103 of hNGF. It is understood that although the epitopes described above relate to human NGF, one of ordinary skill can align the structures of human NGF with the NGF of other species and identify likely counterparts to these epitopes.

In one aspect, antibodies (e.g., human, humanized, mouse, chimeric) that can inhibit NGF may be made by using immunogens that express full length or partial sequence of NGF. In another aspect, an immunogen comprising a cell that overexpresses NGF may be used. Another example of an immunogen that can be used is NGF protein that contains full-length NGF or a portion of the NGF protein.

The anti-NGF antagonist antibodies may be made by any method known in the art. The route and schedule of immunization of the host animal are generally in keeping with established and conventional techniques for antibody stimulation and production, as further described herein. General techniques for production of human and mouse antibodies are known in the art and are described herein.

It is contemplated that any mammalian subject including humans or antibody producing cells therefrom can be manipulated to serve as the basis for production of mammalian, including human, hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) *Nature* 256:495-497 or as modified by Buck, D. W., et al., *In Vitro*, 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the anti-NGF monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies specific for NGF, or a portion thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a human NGF, or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glytaradehyde, succinic anhydride, SOCl2, or R1N=C=NR, where R and R1 are different alkyl groups, can yield a population of antibodies (e.g., monoclonal antibodies).

If desired, the anti-NGF antagonist antibody (monoclonal or polyclonal) of interest may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity, or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to NGF and greater efficacy in inhibiting NGF. It will be apparent to one of skill in the art that one or more polynucleotide changes can be made to the anti-NGF antagonist antibody and still maintain its binding ability to NGF.

There are four general steps to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; and 6,180,370.

A number of "humanized" antibody molecules comprising an antigen-binding site derived from a non-human immunoglobulin have been described, including chimeric antibodies having rodent or modified rodent V regions and their associated complementarity determining regions (CDRs) fused to human constant domains. See, for example, Winter et al. *Nature* 349:293-299 (1991), Lobuglio et al. *Proc. Nat. Acad. Sci. USA* 86:4220-4224 (1989), Shaw et al. *J Immunol.* 138:4534-4538 (1987), and Brown et al. *Cancer Res.* 47:3577-3583 (1987). Other references describe rodent CDRs grafted into a human supporting framework region (FR) prior to fusion with an appropriate human antibody constant domain. See, for example, Riechmann et al. *Nature* 332:323-327 (1988), Verhoeyen et al. *Science* 239:1534-1536 (1988), and Jones et al. *Nature* 321:522-525 (1986). Another reference describes rodent CDRs supported by recombinantly veneered rodent framework regions. See, for example, European Patent Publication No. 0519596. These "humanized" molecules are designed to minimize unwanted immunological response toward rodent anti-human antibody molecules which limits the duration and effectiveness of therapeutic applications of those moieties in human recipients. For example, the antibody constant region can be engineered such that it is immunologically inert (e.g., does not trigger complement lysis). See, e.g. PCT Publication No. PCT/GB99/01441; UK Patent Application No. 9809951.8. Other methods of humanizing antibodies that may also be utilized are disclosed by Daugherty et al., *Nucl. Acids Res.* 19:2471-2476 (1991) and in U.S. Pat. Nos. 6,180,377; 6,054,297; 5,997,867; 5,866,692; 6,210,671; and 6,350,861; and in PCT Publication No. WO 01/27160.

In yet another alternative, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

In an alternative, antibodies may be made recombinantly and expressed using any method known in the art. In another alternative, antibodies may be made recombinantly by phage display technology. See, for example, U.S. Pat. Nos. 5,565,332; 5,580,717; 5,733,743; and 6,265,150; and Winter et al., *Annu. Rev. Immunol.* 12:433-455 (1994). Alternatively, the phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S. and Chiswell, David J., *Current Opinion in Structural Biology* 3:564-571 (1993). Several sources of V-gene segments can be used for phage display. Clackson et al., *Nature* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Mark et al., *J. Mol. Biol.* 222:581-597 (1991), or Griffith et al., *EMBO J.* 12:725-734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." Marks, et al., *Bio/Technol.* 10:779-783 (1992)). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., *Nucl. Acids Res.* 21:2265-2266 (1993). Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen-binding site, i.e., the epitope governs (imprints) the choice of partner. When the process is repeated in order to replace the remaining rodent V domain, a human antibody is obtained (see PCT Publication No. WO 93/06213, published Apr. 1, 1993). Unlike traditional humanization of rodent antibodies by CDR grafting, this technique provides completely human antibodies, which have no framework or CDR residues of rodent origin.

It is apparent that although the above discussion pertains to humanized antibodies, the general principles discussed are applicable to customizing antibodies for use, for example, in dogs, cats, primate, equines and bovines. It is further apparent that one or more aspects of humanizing an antibody described herein may be combined, e.g., CDR grafting, framework mutation and CDR mutation.

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, et al. *Vaccine* 19:2756 (2001); Lonberg, N. and D. Huszar *Int. Rev. Immunol* 13:65 (1995); and Pollock, et al., *J Immunol Methods* 231:147(1999). Methods for making derivatives of antibodies, e.g., humanized, single chain, etc. are known in the art.

Immunoassays and flow cytometry sorting techniques such as fluorescence activated cell sorting (FACS) can also be employed to isolate antibodies that are specific for NGF.

The antibodies can be bound to many different carriers. Carriers can be active and/or inert. Examples of well-known carriers include polypropylene, polystyrene, polyethylene, dextran, nylon, amylases, glass, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation. In some embodiments, the carrier comprises a moiety that targets the myocardium.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors (such as expression vectors disclosed in PCT Publication No. WO 87/04462), which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA also may be modified, for example, by substituting the coding sequence for human heavy and light chain constant domains in place of the homologous murine sequences, Morrison et al., *Proc. Nat. Acad. Sci.* 81:6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of an anti-NGF monoclonal antibody herein.

Anti-NGF antagonist antibodies may be characterized using methods well known in the art. For example, one method is to identify the epitope to which it binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, *Using Antibodies, a Laboratory Manual*, Cold Spring Harbor Laboratory Press, Cold Spring Harbor, N.Y., 1999. In an additional example, epitope mapping can be used to determine the sequence to which an anti-NGF antagonist antibody binds. Epitope mapping is commercially available from various sources, for example, Pepscan Systems (Edelhertweg 15, 8219 PH Lelystad, The Netherlands). The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with an anti-NGF antagonist antibody. In another example, the epitope to which the anti-NGF antagonist antibody binds can be determined in a systematic screening by using overlapping peptides derived from the NGF sequence and determining binding by the anti-NGF antagonist antibody. According to the gene fragment expression assays, the open reading frame encoding NGF is fragmented either randomly or by specific genetic constructions and the reactivity of the expressed fragments of NGF with the antibody to be tested is determined. The gene fragments may, for example, be produced by PCR and then transcribed and translated into protein in vitro, in the presence of radioactive amino acids. The binding of the antibody to the radioactively labeled NGF fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant NGF in which various fragments of the NGF polypeptide have been replaced (swapped) with sequences from a closely related, but antigenically distinct protein (such as another member of the neurotrophin protein family). By assessing binding of the antibody to the mutant NGF, the importance of the particular NGF fragment to antibody binding can be assessed.

Yet another method which can be used to characterize an anti-NGF antagonist antibody is to use competition assays with other antibodies known to bind to the same antigen, i.e., various fragments on NGF, to determine if the anti-NGF antagonist antibody binds to the same epitope as other antibodies. Competition assays are well known to those of skill in the art. Example of antibodies that can be used in the competition assays for the present invention include MAb 911, 912, 938, as described in Hongo, et al., *Hybridoma* 19:215-227 (2000).

An expression vector can be used to direct expression of an anti-NGF antagonist antibody. One skilled in the art is familiar with administration of expression vectors to obtain expression of an exogenous protein in vivo. See, e.g., U.S. Pat. Nos. 6,436,908; 6,413,942; and 6,376,471. Administration of expression vectors includes local or systemic administration, including injection, oral administration, particle gun or catheterized administration, and topical administration. In another embodiment, the expression vector is administered directly to the sympathetic trunk or ganglion, or into a coronary artery, atrium, ventrical, or pericardium.

Targeted delivery of therapeutic compositions containing an expression vector, or subgenomic polynucleotides can also be used. Receptor-mediated DNA delivery techniques are described in, for example, Findeis et al., *Trends Biotechnol*. (1993) 11:202; Chiou et al., *Gene Therapeutics: Methods And Applications Of Direct Gene Transfer* (J. A. Wolff, ed.) (1994); Wu et al., *J. Biol. Chem*. (1988) 263:621;

Wu et al., *J. Biol. Chem.* (1994) 269:542; Zenke et al., *Proc. Natl. Acad. Sci. USA* (1990) 87:3655; Wu et al., *J. Biol. Chem.* (1991) 266:338. Therapeutic compositions containing a polynucleotide are administered in a range of about 100 ng to about 200 mg of DNA for local administration in a gene therapy protocol. Concentration ranges of about 500 ng to about 50 mg, about 1 µg to about 2 mg, about 5 µg to about 500 µg, and about 20 µg to about 100 µg of DNA can also be used during a gene therapy protocol. The therapeutic polynucleotides and polypeptides can be delivered using gene delivery vehicles. The gene delivery vehicle can be of viral or non-viral origin (see generally, Jolly, *Cancer Gene Therapy* (1994) 1:51; Kimura, *Human Gene Therapy* (1994) 5:845; Connelly, *Human Gene Therapy* (1995) 1:185; and Kaplitt, *Nature Genetics* (1994) 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, *Hum. Gene Ther.* (1992) 3:147 can also be employed.

Non-viral delivery vehicles and methods can also be employed, including, but not limited to, polycationic condensed DNA linked or unlinked to killed adenovirus alone (see, e.g., Curiel, *Hum. Gene Ther.* (1992) 3:147); ligand-linked DNA (see, e.g., Wu, *J. Biol. Chem.* (1989) 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0524968. Additional approaches are described in Philip, *Mol. Cell. Biol.* (1994) 14:2411, and in Woffendin, *Proc. Natl. Acad. Sci.* (1994) 91:1581.

Identification of Anti-NGF Antagonist Antibodies

Anti-NGF antagonist antibodies can be identified or characterized using methods known in the art, whereby reduction, amelioration, or neutralization of an NGF biological activity is detected and/or measured. For example, a kinase receptor activation (KIRA) assay described in U.S. Pat. Nos. 5,766,863 and 5,891,650, can be used to identify anti-NGF agents. This ELISA-type assay is suitable for qualitative or quantitative measurement of kinase activation by measuring the autophosphorylation of the kinase domain of a receptor protein tyrosine kinase (hereinafter "rPTK"), e.g. TrkA receptor, as well as for identification and characterization of potential antagonists of a selected rPTK, e.g., TrkA. The first stage of the assay involves phosphorylation of the kinase domain of a kinase receptor, for example, a TrkA receptor, wherein the receptor is present in the cell membrane of an eukaryotic cell. The receptor may be an endogenous receptor or nucleic acid encoding the receptor, or a receptor construct, may be transformed into the cell. Typically, a first solid phase (e.g., a well of a first assay plate) is coated with a substantially homogeneous population of such calls (usually a mammalian call line) so that the cells adhere to the solid phase. Often, the cells are adherent and thereby adhere naturally to the first solid phase. If a "receptor construct" is used, it usually comprises a fusion of a kinase receptor and a flag polypeptide. The flag polypeptide is recognized by the capture agent, often a capture antibody, in the ELISA part of the assay. An analyte, such as a candidate anti-NGF antagonist antibody is then added together with NGF to the wells having the adherent cells, such that the tyrosine kinase receptor (e.g. TrkA receptor) is exposed to (or contacted with) NGF and the analyte. This assay enables identification of antibodies that inhibit activation of TrkA by its ligand NGF. Following exposure to NGF and the analyte, the adhering cells are solubilized using a lysis buffer (which has a solubilizing detergent therein) and gentle agitation, thereby releasing cell lysate which can be subjected to the ELISA part of the assay directly, without the need for concentration or clarification of the cell lysate.

The cell lysate thus prepared is then ready to be subjected to the ELISA stage of the assay. As a first step in the ELISA stage, a second solid phase (usually a well of an ELISA microtiter plate) is coated with a capture agent (often a capture antibody) which binds specifically to the tyrosine kinase receptor, or, in the case of a receptor construct, to the flag polypeptide. Coating of the second solid phase is carried out so that the capture agent adheres to the second solid phase. The capture agent is generally a monoclonal antibody, but, as is described in the examples herein, polyclonal antibodies may also be used. The cell lysate obtained is then exposed to, or contacted with, the adhering capture agent so that the receptor or receptor construct adheres to (or is captured in) the second solid phase. A washing step is then carried out, so as to remove unbound cell lysate, leaving the captured receptor or receptor construct. The adhering or captured receptor or receptor construct is then exposed to, or contacted with, an anti-phosphotyrosine antibody which identifies phosphorylated tyrosine residues in the tyrosine kinase receptor. In one embodiment, the anti-phosphotyrosine antibody is conjugated (directly or indirectly) to an enzyme which catalyses a color change of a non-radioactive color reagent. Accordingly, phosphorylation of the receptor can be measured by a subsequent color change of the reagent. The enzyme can be bound to the anti-phosphotyrosine antibody directly, or a conjugating molecule (e.g., biotin) can be conjugated to the anti-phosphotyrosine antibody and the enzyme can be subsequently bound to the anti-phosphotyrosine antibody via the conjugating molecule. Finally, binding of the anti-phosphotyrosine antibody to the captured receptor or receptor construct is measured, e.g., by a color change in the color reagent.

The anti-NGF antagonist antibody can also be identified by incubating a candidate agent with NGF and monitoring any one or more of the following characteristics: (a) binding to NGF; (b) inhibiting NGF biological activity or downstream pathways mediated by NGF signaling function; (c) inhibiting, blocking or decreasing NGF receptor activation (including TrkA dimerization and/or autophosphorylation);

(d) increasing clearance of NGF; (e) treating or preventing any aspect of post-surgical pain; (f) inhibiting (reducing) NGF synthesis, production or release; (g) enhancing recovery from surgery. In some embodiments, an anti-NGF antagonist antibody is identified by incubating a candidate agent with NGF and monitoring binding and/or attendant reduction or neutralization of a biological activity of NGF. The binding assay may be performed with purified NGF polypeptide(s), or with cells naturally expressing, or transfected to express, NGF polypeptide(s). In one embodiment, the binding assay is a competitive binding assay, where the ability of a candidate antibody to compete with a known anti-NGF antagonist for NGF binding is evaluated. The assay may be performed in various formats, including the ELISA format. In other embodiments, an anti-NGF antagonist antibody is identified by incubating a candidate agent with NGF and monitoring binding and attendant inhibition of trkA receptor dimerization and/or autophosphorylation.

Following initial identification, the activity of a candidate anti-NGF antagonist antibody can be further confirmed and refined by bioassays, known to test the targeted biological activities. Alternatively, bioassays can be used to screen candidates directly. For example, NGF promotes a number of morphologically recognizable changes in responsive cells. These include, but are not limited to, promoting the differentiation of PC12 cells and enhancing the growth of neurites from these cells (Urfer et al., *Biochem.* 36:4775-4781 (1997); Tsoulfas et al., *Neuron* 10:975-990 (1993)), promoting neurite outgrowth from explants of responsive sensory and sympathetic ganglia (Levi-Montalcini, R. and Angeletti, P. Nerve growth factor. *Physiol. Rev.* 48:534-569, 1968) and promoting the survival of NGF dependent neurons such as embryonic dorsal root ganglion, trigeminal ganglion, or sympathetic ganglion neurons (e.g., Chun & Patterson, Dev. Biol. 75:705-711, (1977); Buchman & Davies, *Development* 118:989-1001 (1993). Thus, the assay for inhibition of NGF biological activity entail culturing NGF responsive cells with NGF plus an analyte, such as a candidate anti-NGF antagonist antibody. After an appropriate time the cell response will be assayed (cell differentiation, neurite outgrowth or cell survival).

The ability of a candidate anti-NGF antagonist antibody to block or neutralize a biological activity of NGF can also be assessed by monitoring the ability of the candidate agent to inhibit NGF mediated survival in the embryonic rat dorsal root ganglia survival bioassay as described in Hongo et al., *Hybridoma* 19:215-227 (2000).

Compositions

The compositions used in the methods of the invention comprise an effective amount of an anti-NGF antagonist antibody. Examples of such compositions, as well as how to formulate, are also described in an earlier section and below. In one embodiment, the composition comprises a NGF antagonist. In another embodiment, the composition comprises one or more anti-NGF antagonist antibodies. In other embodiments, the anti-NGF antagonist antibody recognizes human NGF. In still other embodiments, the anti-NGF antagonist antibody is humanized (such as antibody E3 described herein). In some embodiments, the anti-NGF antagonist antibody binds NGF and does not significantly cross-react with related neurotrophins (such as NT3, NT4/5, and/or BDNF). In still other embodiment, the anti-NGF antagonist antibody comprises a constant region that does not trigger an unwanted or undesirable immune response, such as antibody-mediated lysis or ADCC. In other embodiments, the anti-NGF antagonist antibody comprises one or more CDR(s) of antibody E3 (such as one, two, three, four, five, or, in some embodiments, all six CDRs from E3). In some embodiments, the anti-NGF antagonist antibody is human.

It is understood that the compositions can comprise more than one anti-NGF antagonist antibody (e.g., a mixture of anti-NGF antagonist antibodies that recognize different epitopes of NGF). Other exemplary compositions comprise more than one anti-NGF antagonist antibodies that recognize the same epitope(s), or different species of anti-NGF antagonist antibodies that bind to different epitopes of NGF.

The composition used in the present invention can further comprise pharmaceutically acceptable carriers, excipients, or stabilizers (*Remington: The Science and practice of Pharmacy* 20th Ed. (2000) Lippincott Williams and Wilkins, Ed. K. E. Hoover.), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

The anti-NGF antagonist antibody and compositions thereof can also be used in conjunction with other agents that serve to enhance and/or complement the effectiveness of the agents.

Kits

The invention also provides kits for use in the instant methods. Kits of the invention include one or more containers comprising an anti-NGF antagonist antibody (such as a humanized antibody, such as antibody E3 described herein) and instructions for use in accordance with any of the methods of the invention described herein. Generally, these instructions comprise a description of administration of the anti-NGF antagonist antibody to treat, ameliorate or prevent post-surgical pain according to any of the methods described herein. The kit may further comprise a description of selecting an individual suitable for treatment based on identifying whether that individual has post-surgical pain or whether the individual is at risk of post-surgical pain. In still other embodiments, the instructions comprise a description of administering an anti-NGF antagonist antibody to an individual at risk of post-surgical pain.

In some embodiments, the antibody is a humanized antibody (such as antibody E3 described herein). In some embodiments, the antibody is human. In other embodiments, the antibody is a monoclonal antibody. In still other embodiments. In some embodiment, the antibody comprises one or more CDR(s) of antibody E3 (such as one, two, three, four, five, or, in some embodiments, all six CDRs from E3).

The instructions relating to the use of an anti-NGF antagonist antibody generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, ameliorating and/or preventing post-surgical pain. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-NGF antagonist antibody. The container may further comprise a second pharmaceutically active agent.

Kits may optionally provide additional components such as buffers and interpretive information. Normally, the kit comprises a container and a label or package insert(s) on or associated with the container.

Administration of an Anti-NGF Antagonist Antibody and Assessment of Treatment

The anti-NGF antagonist antibody can be administered to an individual via any suitable route. It should be apparent to a person skilled in the art that the examples described herein are not intended to be limiting but to be illustrative of the techniques available. Accordingly, in some embodiments, the anti-NGF antagonist antibody is administered to a individual in accord with known methods, such as intravenous administration, e.g., as a bolus or by continuous infusion over a period of time, by intramuscular, intraperitoneal, intracerebrospinal, subcutaneous, intra-articular, sublingually, intrasynovial, via insufflation, intrathecal, oral, inhalation or topical routes. Administration ca be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution. Alternatively, anti-NGF antagonist antibody can be aerosolized using a fluorocarbon formulation and a metered dose inhaler, or inhaled as a lyophilized and milled powder.

In one embodiment, an anti-NGF antagonist antibody is administered via site-specific or targeted local delivery techniques. Examples of site-specific or targeted local delivery techniques include various implantable depot sources of the anti-NGF antagonist antibody or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Various formulations of an anti-NGF antagonist antibody may be used for administration. In some embodiments, the anti-NGF antagonist antibody may be administered neat. In some embodiments, anti-NGF antagonist antibody and a pharmaceutically acceptable excipient may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in *Remington, The Science and Practice of Pharmacy* 20th Ed. Mack Publishing (2000).

In some embodiments, these agents are formulated for administration by injection (e.g., intraperitoneally, intravenously, subcutaneously, intramuscularly, etc.). Accordingly, these agents can be combined with pharmaceutically acceptable vehicles such as saline, Ringer's solution, dextrose solution, and the like. The particular dosage regimen, i.e., dose, timing and repetition, will depend on the particular individual and that individual's medical history.

An anti-NGF antibody can be administered using any suitable method, including by injection (e.g., intraperitoneally, intravenously, subcutaneously, intramuscularly, etc.). Anti-NGF antibodies can also be administered via inhalation, as described herein. Generally, for administration of anti-NGF antibodies, an initial candidate dosage can be about 2 mg/kg. For the purpose of the present invention, a typical daily dosage might range from about any of 3 μg/kg to 30 μg/kg to 300 μg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to reduce post-surgical pain. An exemplary dosing regimen comprises administering an initial dose of about 2 mg/kg, followed by a weekly maintenance dose of about 1 mg/kg of the anti-NGF antibody, or followed by a maintenance dose of about 1 mg/kg every other week. However, other dosage regimens may be useful, depending on the pattern of pharmacokinetic decay that the practitioner wishes to achieve. For example, in some embodiments, dosing from one-four time a week is contemplated. The progress of this therapy is easily monitored by conventional techniques and assays. The dosing regimen (including the NGF antagonist(s) used) can vary over time.

For the purpose of the present invention, the appropriate dosage of an anti-NGF antagonist antibody will depend on the anti-NGF antagonist antibody (or compositions thereof) employed, the type and severity of the pain to be treated, whether the agent is administered for preventive or therapeutic purposes, previous therapy, the patient's clinical history and response to the agent, and the discretion of the attending physician. Typically the clinician will administer an anti-NGF antagonist antibody, until a dosage is reached that achieves the desired result. Dose and/or frequency can vary over course of treatment.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of pain. Alternatively, sustained continuous release formulations of anti-NGF antagonist antibodies may be appropriate. Various formulations and devices for achieving sustained release are known in the art.

In one embodiment, dosages for an anti-NGF antagonist antibody may be determined empirically in individuals who have been given one or more administration(s) of an anti-NGF antagonist antibody. Individuals are given incremental dosages of an anti-NGF antagonist antibody. To assess efficacy of an anti-NGF antagonist antibody, an indicator of pain can be followed.

Administration of an anti-NGF antagonist antibody in accordance with the method in the present invention can be continuous or intermittent, depending, for example, upon the recipient's physiological condition, whether the purpose of the administration is therapeutic or prophylactic, and other factors known to skilled practitioners. The administration of an anti-NGF antagonist antibody may be essentially continuous over a preselected period of time or may be in a series of spaced dose, e.g., either before, during, or after developing pain; before; during; before and after; during and after; before and during; or before, during, and after developing pain. Administration can be before, during and/or after wound, incision, trauma, surgery, and any other event likely to give rise to post-surgical pain.

In some embodiments, more than one anti-NGF antagonist antibody may be present. At least one, at least two, at least three, at least four, at least five different, or more anti-NGF antagonist antibody can be present. Generally, those anti-NGF antagonist antibodies have complementary activities that do not adversely affect each other. An antagonist anti-NGF antibody can also be used in conjunction with other NGF antagonists, including one or more of the following NGF antagonists: an anti-sense molecule directed to an NGF (including an anti-sense molecule directed to a nucleic acid encoding NGF), an NGF inhibitory compound, an NGF structural analog, a dominant-negative mutation of a TrkA receptor that binds an NGF, an anti-TrkA antibody, an anti-p75 antibody and a kinase inhibitor. An anti-NGF antagonist antibody can also be used in conjunction with other agents that serve to enhance and/or complement the effectiveness of the agents.

Therapeutic formulations of the anti-NGF antagonist antibody used in accordance with the present invention are prepared for storage by mixing an antibody having the desired degree of purity with optional pharmaceutically acceptable carriers, excipients or stabilizers (*Remington, The Science and Practice of Pharmacy* 20th Ed. Mack Publishing (2000)), in the form of lyophilized formulations or aqueous solutions. Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosacchandes, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Liposomes containing the anti-NGF antagonist antibody are prepared by methods known in the art, such as described in Epstein, et al., *Proc. Natl. Acad. Sci. USA* 82:3688 (1985); Hwang, et al., *Proc. Natl. Acad. Sci. USA* 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington, The Science and Practice of Pharmacy* 20th Ed. Mack Publishing (2000).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or 'poly(v nylalcohol)), polylactides (U.S. Pat. No. 3,773,919), copolymers of L-glutamic acid and 7 ethyl-Lglutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3hydroxybutyric acid.

The formulations to be used for in vivo administration must be sterile. This is readily accomplished by, for example, filtration through sterile filtration membranes. Therapeutic anti-NGF antagonist antibody compositions are generally placed into a container having a sterile access port, for example, an intravenous solution bag or vial having a stopper pierceable by a hypodermic injection needle.

The compositions according to the present invention may be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example gylcerol or glucose, to adjust the tonicity of the emulsion. Suitable emulsions will typically contain up to 20% oil, for example, between 5 and 20%. The fat emulsion can comprise fat droplets between 0.1 and 1.0 .µm, particularly 0.1 and 0.5 .µm, and have a pH in the range of 5.5 to 8.0.

The emulsion compositions can be those prepared by mixing a nerve growth factor antagonist with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Treatment efficacy can be assessed by methods well-known in the art.

EXAMPLES

The following Examples are provided to illustrate but not limit the invention.

Example 1

Anti-NGF Monoclonal Antibody is Effective in Treating Post-Surgical Pain

We used a pain model that mimics post surgical pain to assess the efficacy of treatment with anti-NGF antibody 911 (a mouse monoclonal antibody; see Hongo, et al., *Hybridoma* 19:215-227 (2000). Each experiment involved 16 animals (n=8 per group). The anti-NGF antibody was injected intra peritoneal (i.p.) at various concentrations per experiment (35 or 7 milligrams per kilogram) 15 hours pre-incision. The control group received no antibody but was injected i.p. with a saline solution.

Animals. Male Sprague Dawley rats weighting between 220-240 grams were purchased from Harlan (San Diego) and acclimated to the animal facility for one week prior to surgery.

Surgery. The surgery was based on the procedure described by Brennan, et al. *Pain* 64:493-501 (1996). Animals were anesthetized with a 2% isoflurane in air mixture that was maintained during surgery via a nose cone. The plantar surface of the right hind paw was prepared with a povidone-iodine pad, and a 1-cm central longitudinal incision was made through skin and fascia, starting 0.5 cm from the edge of the heel and extending toward the toes. Measurements were made with a ruler with the foot held in a flexed position. The plantaris muscle was elevated using curved forceps and incised longitudinally. The muscle was incised through its full depth, between the origin and insertion. Bleeding was controlled throughout surgery by pressure applied through a gauze pad. The wound was closed with two mattress sutures (5-0 ethilon black monofilament). These sutures were knotted 5-6 times, with the first knot loosely tied. The wound site was swabbed with bacitracin solution. Animals were allowed to recover and rest in clean cages for two hours or more before behavioral testing began.

Figure 1:
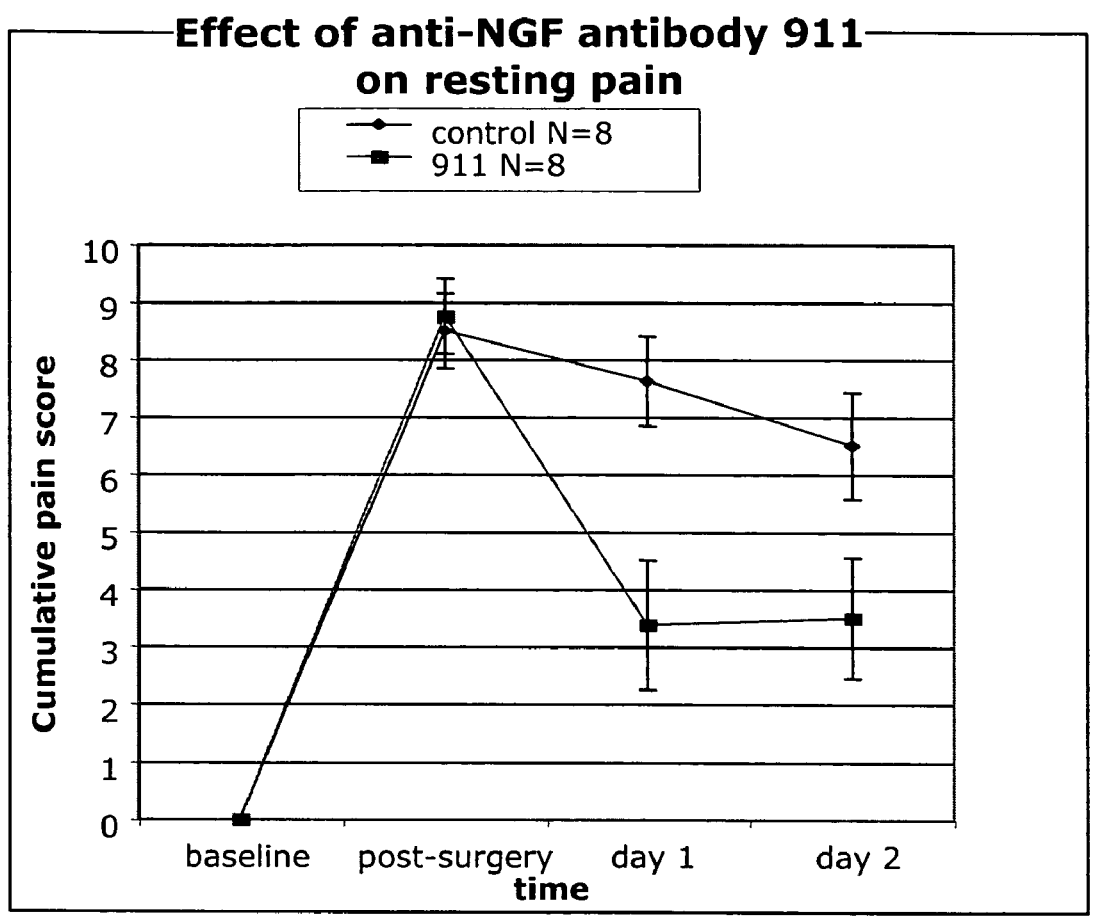

Evaluating resting pain. A cumulative pain score was used to assess pain related to weight bearing. Animals were placed on a plastic mesh (grid: 8 mm2) in clear plastic cages that were elevated on a platform (h: 18") allowing inspection of the underside of their paws. After a 20 minute acclimation period, weight bearing was assessed on a scale of 0 to 2. A score of 0 was given if the paw was blanched or pressed against the mesh, indicating full weight bearing. A score of 1 was given if the paw was favored with the skin just touching the mesh, with no blanching or indentation of the skin. A score of 2 was given if the paw was held completely off the mesh. Flinching the paw was considered a 2 if the rat was still at rest. Each animal was observed for 1 minute every 5 minutes for 30 minutes. The sum of 6 scores (0-12) obtained during ½ hour was used to assess pain in the incised foot. Frequency of scores of 2 was also calculated and used to assess the incidence of severe pain or total guarding of the paw by the animal. Each animal was tested 24 hours before surgery (baseline), and 2 h, 24 h, 48 h, and 72 h postoperatively. The results of this experiment are shown in FIG. 1, which depicts the cumulative resting pain score observed in animals treated with 35 mg/kg of anti-NGF mouse antibody 911. These results demonstrated that treatment with anti-NGF antibody significantly reduced post-surgical resting pain. Weight bearing was a good correlate of how willing the animal was to use the limb, and therefore was an effective measure of pain relief.

Evaluation of mechanically evoked pain using tactile allodynia. Tactile allodynia was measured with Semmes-Weinstein von Frey hairs (Stoelting, Wood Dale, Ill.). Animals were placed into 12 mm plastic mesh bottom cages, elevated on a platform (h: 18") allowing access to the underside of their paws. The animals were habituated to this environment (over 1-2 days the week prior) before the start of the experiment. After a 15 minute acclimation period, tactile allodynia was tested by touching the skin, medial and proximal to the entry point of the incision, on the heel of the animal's hind paw with von Frey hairs in ascending order of force until a paw-withdrawal response was elicited. Von Frey numbers 4.08 to 5.46 were used; each number correlates with a force in grams, as described below. Each von Frey hair was applied to the surface at a right angle, bending the hair for 2 s, or until a response occurred. Once a withdrawal response was established, the paw was retested for two more trials, starting with the next descending von Frey hair until no response occurred.

Figure 3:
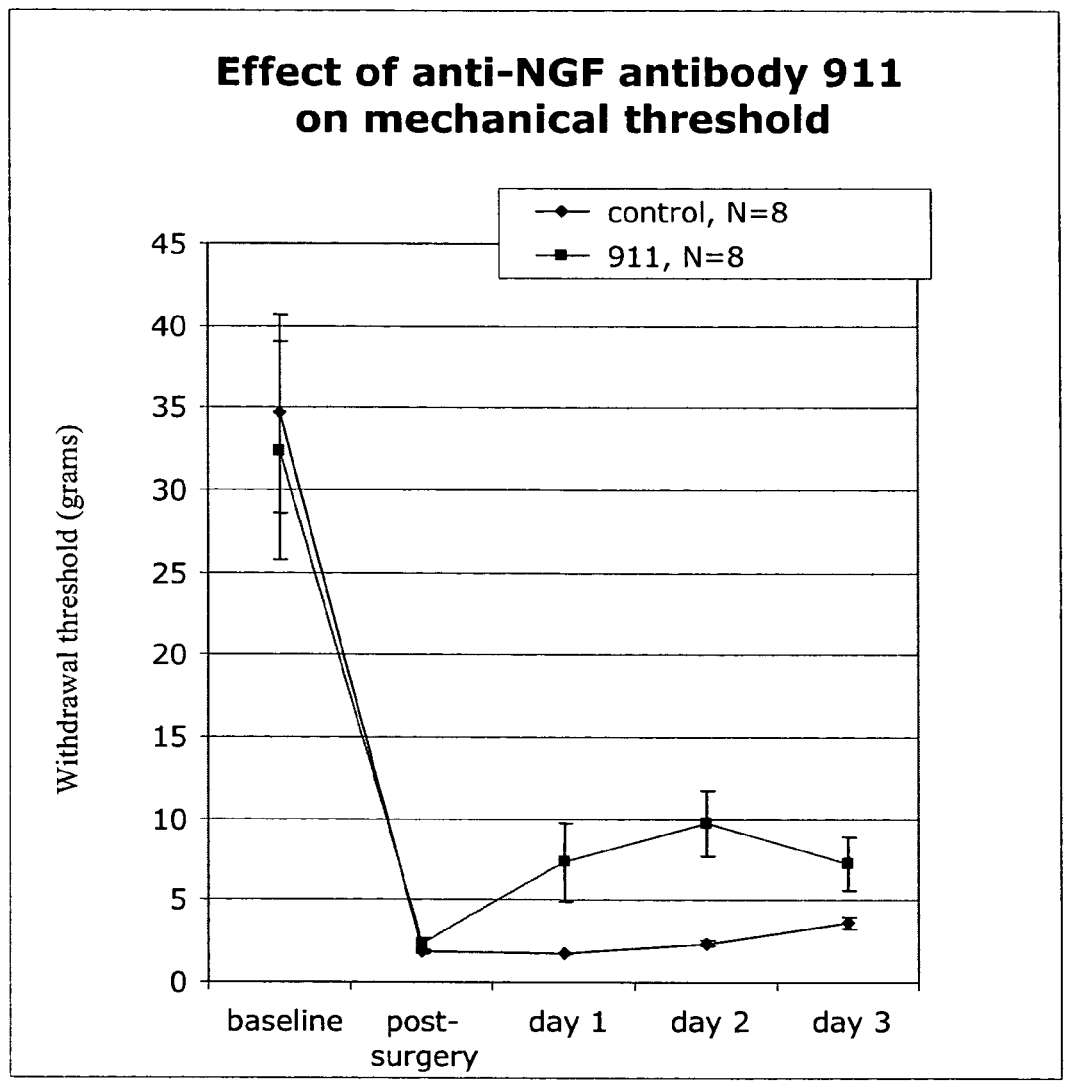

The lowest amount of force required to elicit a response over the three trials was recorded as withdrawal threshold in grams. The highest force of 29 g lifted the paw as well as eliciting a response, thus representing the cut-off point. If no response was detected, the next ascending filament "5.88" was recorded. Both left and right paws were tested in this manner. Each animal was tested 24 hours before surgery (baseline), and 2 h, 24 h, 48 h, and 72 h postoperatively. Tactile allodynia was tested after resting pain scoring. The results of this experiment are shown in FIG. 3, which provides the cumulative score in response to mechanical stimulation in animals treated with 7 mg/kg of anti-NGF antibody 911. These results demonstrated that treatment with anti-NGF antibody decreased post-surgical mechanically-evoked pain.

Figure 2:
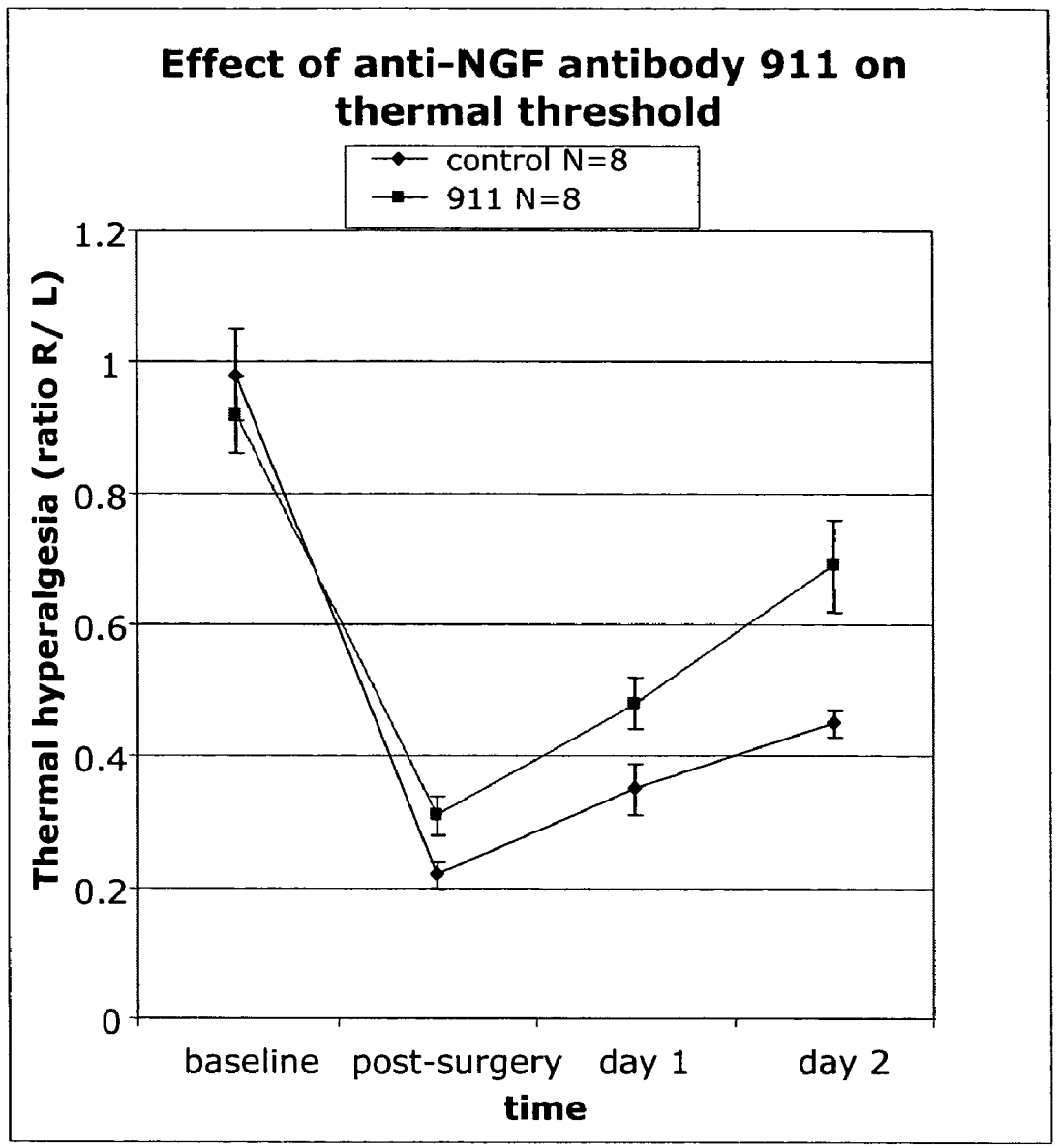

Evaluation of thermal hyperalgesia. Thermal hyperalgesia was assessed by the rat plantar test (Ugo Basile, Italy) following a modified method of Hargreaves, et al. (1988). Rats were habituated to the apparatus that consisted of four individual plexiglass boxes on an elevated glass table. A mobile radiant heat source was located under the table and focused onto the hind paw. While the animal is still, but not sleeping, the button on the control box is depressed, the radiant heat source comes on and the time taken for the animal to withdraw from the heat source is automatically recorded. This paw withdrawal latency (PWL) is detected by a light detector embedded in the radiant heat source that senses the movement of the rat paw by a change in reflectance of the radiant source. Paw Withdrawal Latencies, in seconds, were recorded. There was an automatic cut-off point of 22.5 s to prevent tissue damage. PWL were taken three to four times for both hind paws of each animal, the mean of which represented base lines for right and left hind paws. The results are presented as the ratio of score measured in the right paw (site of surgery) and the left paw. The apparatus was calibrated once (at the beginning of the study) and set to intensity of 40 to give a normal PWL of approximately 6 seconds. Each animal was tested 24 hours before surgery (baseline), and 3 h, 24 h, 48 h, and 72 h postoperatively. Thermal hyperalgesia measurements were taken after tactile allodynia measurements. The results of this experiment are shown in FIG. 2, which depicts the cumulative score observed in animals treated with 35 mg/kg of anti-NGF antibody 911 in response to thermal stimulation. These results demonstrated that treatment with anti-NGF antibody significantly reduced post-surgical thermal hyperalgesia.

Example 2

Treatment of Post-Surgical Pain Using a Humanized Anti-NGF Antibody and Comparison with Opioid Treatment of Post-Surgical Pain Effect of a humanized anti-NGF antibody designated E3 on post-surgical pain was tested in an animal model for post-surgical pain as described in Example 1. The E3 antibody comprises the human heavy chain IgG2a constant region containing the following mutations: A330P331 to S330S331 (amino acid numbering with reference to the wildtype IgG2a sequence; see Eur. J. Immunol. (1999) 29:2613-2624); the human light chain kappa constant region; and the heavy and light chain variable regions shown in Tables 1 and 2.

The anti-NGF antibody was injected intra peritoneal (i.p.) at various concentrations of the antibody (0.004, 0.01, 0.02, 0.1, 0.6, and 1 mg per kilogram of animal weight) at 15 hours pre-incision. The negative control group received no antibody but was injected i.p. with a saline solution. Fentanyl at 0.01 mg/kg was injected i.p. as a positive control 30 minutes before testing at 24 hours post-surgery. Each experiment involved 8 animals (n=8 per group) for each condition, and the control group had 56 animals. Surgery was performed and a cumulative pain score was measured as described in Example 1, except that the male Sprague Dawley rats were purchased from Harlan (Wisconsin). Resting pain was evaluated twenty-four hours after the surgery as described in Example 1.

Figure 4:
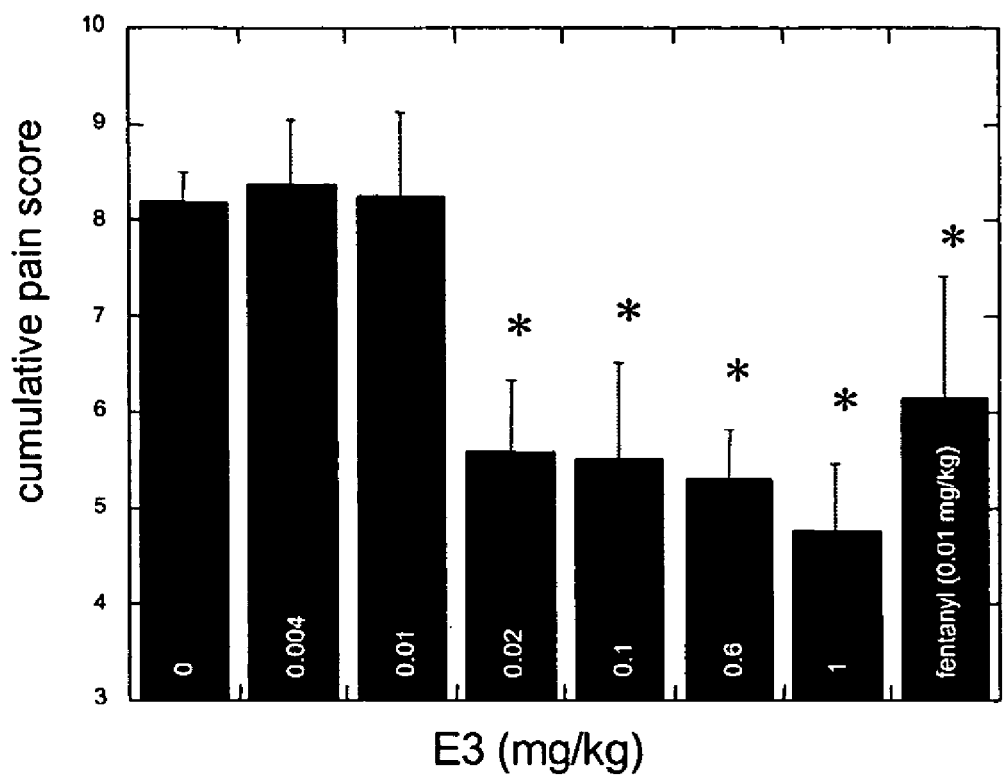
FIG. 4 is a graph depicting resting pain assessed 24 hours after surgery and showing that treatment with 0.02 mg/kg, 0.1 mg/kg, 0.6 mg/kg, or 1 mg/kg humanized anti-NGF antibody E3 reduced pain. "*" indicates a statistically significant difference ($p<0.5$) from the negative control.

As shown in FIG. 4, humanized anti-NGF antibody E3 significantly reduced resting pain ($p<0.05$) after surgery when administered at 0.02 mg/kg to 1 mg/kg dosage. A "*" denotes a significantly significant difference from control ($p<0.05$). Treatment with 0.02 mg/kg alleviated pain behavior at least as effectively as treatment with 0.01 mg/kg fentanyl. This dose of fentanyl is 10 times the normal human dose of this potent opioid.

Example 3

Figure 5:
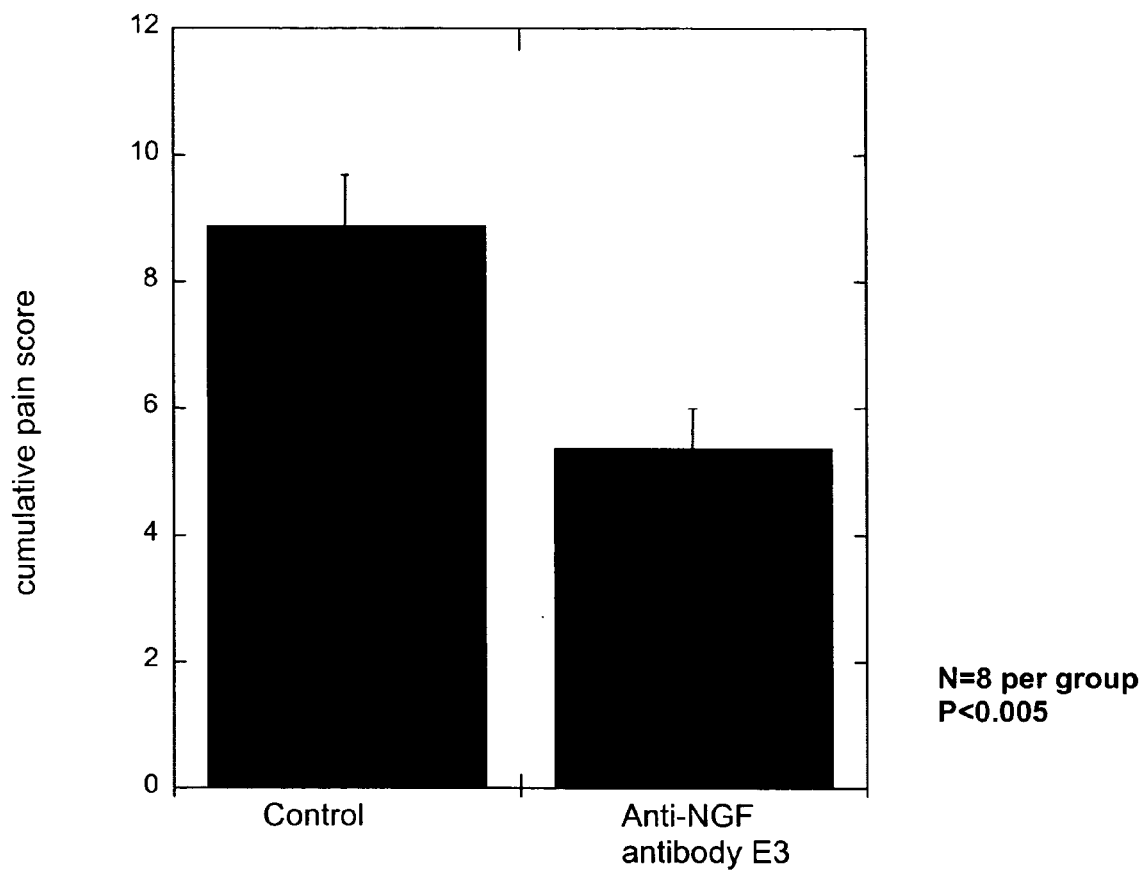
FIG. 5 is a graph depicting resting pain assessed 24 hours after surgery and showing that treatment with 0.5 mg/kg of humanized anti-NGF antibody E3 significantly ($p<0.005$) reduced resting pain when injected two hours after surgery.

Pre-Surgery and Post-Surgery Treatment of Post-Surgical Pain with an Anti-NGF Antibody Efficacy of an anti-NGF antibody in reducing post-surgical pain when administered post-incisionally was tested in the post-surgical pain animal model described in Example 1, using male Sprague Dawley rats purchased from Harlan (Wisconsin). Humanized anti-NGF antibody E3 (0.5 mg/kg) were injected intravenously (i.v.) two hours after incision. The control group received no antibody but was injected i.v. with a saline solution. Surgery was performed and resting pain expressed as a cumulative pain score was assessed 24 hours after surgery as described in Example 1. As shown in FIG. 5, treatment with anti-NGF antibody significantly ($p<0.05$) reduced resting pain at twenty-four hours after incision when the antibody was administered 2 hours post-incision. These results demonstrated that anti-NGF effectively alleviated post-surgical pain when administered after surgery.

Efficacy of an anti-NGF antibody in reducing post-surgical pain when administered 14 days or 21 days pre-incision was tested in the animal model described in Example 1, using male Sprague Dawley rats purchased from Harlan (Wisconsin). Anti-NGF mouse monoclonal antibody 911 was injected i.p. at various concentrations (1 mg/kg or 5 mg/kg) at 14 days or 21 days pre-incision. The control group was injected i.p. with a saline solution. Surgery was performed and resting pain expressed as a cumulative pain score was assessed 24 hours after surgery as described in Example 1. As shown in FIGS. 6 and 7, anti-NGF antibody 911 significantly reduced resting pain at the 5 mg/kg dosage when administered 14 days before surgery, and reduced resting pain when injected 21 days prior to surgery.

Example 4

Treatment with Anti-NGF Antibody Shows No Effect on Wound Healing

There are suggestions in the scientific literature that treatment with excess NGF can promote wound healing in diabetic animals (Matsuda et al. (1998) J Exp Med 187(3): 297-30) and corneal ulcers and skin (Lambiase et al., (2003) Arch Ital Biol. 141(2-3):141-8). To determine whether use of anti-NGF antibody would impair wound healing, the effect of anti-NGF antibody treatment on wound healing was tested in rats.

Male Sprague-Dawley rats weighing 250-350 grams were purchased from Harlan (Wisconsin) were brought into the facility and acclimated for at least one week. Animals were anaesthetized with isoflurane and the dorsal surface (back) was shaved and cleaned with povidone iodine followed by an alcohol pad. A 2.5 cm incision through the skin was made on the midline between the scapulae. Bleeding was controlled with pressure with a gauze pad. The wound was closed with four single 4-0 ethilon sutures and the animals were allowed to recover. Animals were then divided into three groups: one group receiving a single does of mouse monoclonal anti-NGF antibody 911 at the time of surgery (1 mg/kg, i.p.); one group receiving Ketorolac (5 mg/kg daily for five days starting the day of surgery, intramuscularly (IM0) as a positive control; and a saline treated control group (negative control). Ketorolac is known to inhibit wound healing. Haws et al. (1996) *Ann Plast Surg.* 37(2): 147-51; Gerstenfeld et al. (2003) *J Orthop Res.* 21(4):670-5.

The area of the incision was examined and photographed daily starting at day one post surgery. Sutures were removed on day 2 post surgery. Incisions were scored as "intact" if the entire incision remained closed, and "failed" if some or all of the incision re-opened. Results were expressed as the proportion of intact wounds (i.e., the number of intact wounds divided by the total number of animals scored).

As shown in FIG. 8, wound healing of animals treated with anti-NGF antibody 911 was not significantly different from that of animals treated with saline. Thus, anti-NGF treatment showed no apparent effect on wound healing. By contrast, wound healing was significantly inhibited in ketorolac treated animals when compared to saline or anti-NGF antibody 911 treated animal ($p<0.0005$).

The histological appearance of the healed wounds was also examined in three rats treated with anti-NGF antibody and three rats treated with saline. 21 days post incision, the animals were sacrificed and skin sample including the area of the incision was fixed in formalin, embedded in paraffin and sectioned across the site of the incision. These sections were treated with anti-NGF antibody or saline stained with hematoxylin and eosin and examined by a veterinary pathologist blinded to the animals' treatment. No abnormalities of wound healing were seen in either group of rats.

Example 5

Comparison of Post-Surgical Pain in Animals Treated with Anti-NGF Antibody or Isotype Matched Control Antibody In order to show that the analgesic effect of the anti-NGF antibody required the inhibition of NGF, effectiveness of anti-NGF mouse antibody 911 in treating post-surgical pain was compared with effectiveness of the same dose of an isotype-matched control murine antibody that is immunoreactive with the *Drosophila* protein amnesiac. The experiment was performed as in Example 1, except that the Sprague-Dawley rats were purchased from Harlan (Wisconsin). Rats were treated IP fifteen hours before surgery with 1 mg/kg of either anti-NGF antibody 911 (marked "911" in the Figure) or isotype matched anti-amnesiac antibody (marked "amn ab" in the Figure). At twenty-four hours after surgery, resting pain (cumulative pain score) was assessed by an observer blinded to the treatment of the animals. As shown in FIG. 9, treatment with anti-NGF antibody 911 significantly ($p<0.005$) reduced the resting pain compared to animals treated with the amnesiac antibody. These results demonstrated that the analgesic effect of treatment with anti-NGF antibodies is specific.

Although the foregoing invention has been described in some detail by way of illustration and example for purposes of clarity of understanding, the descriptions and examples should not be construed as limiting the scope of the invention.

We claim:

1. A method for treating post-surgical pain in a human subject comprising administering to the subject in need of such treatment an effective amount of an anti-nerve growth factor (NGF) antagonist antibody, whereby the post-surgical pain in the subject is treated.

2. The method of claim 1, wherein the post-surgical pain comprises resting pain, and wherein the resting pain is ameliorated.

3. The method of claim 1, wherein the post-surgical pain comprises mechanically-induced pain, and wherein the mechanically-induced pain is ameliorated.

4. The method of claim 1, wherein the anti-NGF antagonist antibody is a human antibody.

5. The method of claim 1, wherein the anti-NGF antagonist antibody is a humanized antibody.

6. The method of claim 1, wherein the anti-NGF antagonist antibody binds human NGF.

7. The method of claim 6, wherein the anti-NGF antagonist antibody binds human NGF with a binding affinity of about 0.1 nM or less than about 0.1 nM.

8. The method of claim 1, wherein the post-surgical pain comprises resting pain and mechanically-induced pain, and wherein the resting pain and mechanically-induced pain are ameliorated.

9. The method of claim 1, wherein the post-surgical pain comprises thermally-induced pain, and wherein the thermally-induced pain is ameliorated.

10. The method of claim 1, wherein the post-surgical pain comprises resting pain, mechanically-induced pain, and thermally-induced pain, and wherein the resting pain, mechanically-induced pain, and thermally-induced pain are ameliorated.

11. The method of claim 1, wherein wound healing is not significantly inhibited.

* * * * *